(12) United States Patent
Annapragada et al.

(10) Patent No.: US 7,785,568 B2
(45) Date of Patent: Aug. 31, 2010

(54) COMPOSITIONS AND METHODS FOR ENHANCING CONTRAST IN IMAGING

(75) Inventors: Ananth Annapragada, Manvel, TX (US); Ravi V. Bellamkonda, Marietta, GA (US); Eric Hoffman, Iowa City, IA (US); Chandra Vijayalakshmi, Manvel, TX (US)

(73) Assignee: Marval Biosciences, Inc., Houston, TX (US)

( * ) Notice: Subject to any disclaimer, the term of this patent is extended or adjusted under 35 U.S.C. 154(b) by 821 days.

(21) Appl. No.: 11/595,808

(22) Filed: Nov. 10, 2006

(65) Prior Publication Data

US 2007/0212303 A1    Sep. 13, 2007

Related U.S. Application Data

(63) Continuation-in-part of application No. 10/830,190, filed on Apr. 21, 2004, now Pat. No. 7,713,517.

(51) Int. Cl.
   A61K 49/04   (2006.01)
   A61K 49/00   (2006.01)

(52) U.S. Cl. .......................................... 424/9.1; 424/9.4

(58) Field of Classification Search .................. 424/9.4
   See application file for complete search history.

(56) References Cited

U.S. PATENT DOCUMENTS

| | | | |
|---|---|---|---|
| 5,049,389 A | | 9/1991 | Radhakrishnan |
| 5,312,615 A | | 5/1994 | Schneider et al. |
| 5,676,928 A | | 10/1997 | Klaveness et al. |
| 5,869,023 A | * | 2/1999 | Ericcson et al. ............. 424/9.36 |
| 6,217,849 B1 | | 4/2001 | Tournier et al. |
| 6,468,505 B1 | * | 10/2002 | Lang et al. ................ 424/9.321 |
| 2003/0190284 A1 | | 10/2003 | Annapragada et al. |

FOREIGN PATENT DOCUMENTS

EP       1121102       8/2001

OTHER PUBLICATIONS

Kao et al., Long-residence-time nano-scale liposomal iohexol for X-ray-based blood pool imaging, Academic Radiology, May 2003, pp. 475-483.
Leike Ju, Sachse A, Rupp K: Characterization of continuously extruded iopromide-carrying liposomes for computed tomography blood-pool imaging, Invest Radiol 2001; 36(6):303-8.
VP Torchilin, J. Narula, E. Halpern, B. AN Khaw Biochim, Biophys. Acta 1279 (1996) 75-83.
Vera DR, Mattrey RF: A molecular CT blood pool, contast agent. Acad Radiol 2002; 9(7):784-92.
Sachse A, Leike JU, Schneider T, Wagner SE, Rossling GL, Krause W, Brandl M.: Biodistribution and computed tomography blood-pool imaging properties of polyethylene glycol-coated iopromide-carrying liposomes. Invest Radiol. Jan. 1997; 32(1);44-50.
Srinath, P. and P.V. Diwan: Stealth liposomes—an overview, Indian J. of Pharmacology 1994, v. 26, pp. 179-184.
Torchilin, V.P., PEG-based micelles as carriers of contrast agents for different imaging modalities, Advanced Drug Delivery Reviews, 2002, v. 54, pp. 235-252.
Written Opinion and search report from related PCT Application No. PCT/US05/00876.
U.S. Appl. No. 11/568,936, filed Nov. 10, 2006.

* cited by examiner

*Primary Examiner*—Michael G Hartley
*Assistant Examiner*—Melissa Perreira
(74) *Attorney, Agent, or Firm*—Benjamen E. Kern

(57) ABSTRACT

Example compositions of liposomes with hydrophilic polymers on their surface, and containing relatively high concentrations of contrast-enhancing agents for computed tomography are provided. Example pharmaceutical compositions of such liposomes, when administered to a subject, provide for increased contrast of extended duration, as measured by computed tomography, in the bloodstream and other tissues of the subject. Also provided are example methods for making the liposomes containing high concentrations of contrast-enhancing agents, and example methods for using the compositions.

4 Claims, 13 Drawing Sheets

COMPOSITIONS AND METHODS FOR ENHANCING CONTRAST IN IMAGING

BACKGROUND

Some medical X-ray imaging techniques can detect variations in contrast of regions of interest in a subject, including different organs, tissues, cells and the like. To increase the contrast of regions of interest, some of the imaging techniques utilize the administration of one or more contrast-enhancing agents to a subject. The contrast-enhancing agents can accentuate existing differences in contrast between different areas of interest, or can produce differences in contrast where such differences do not exist without use of the agents.

There have been advancements in medical X-ray imaging, specifically relating to the instruments or machines used to detect the differences in contrast. These advancements include increases in the speed of the instruments, increases in the resolution of the instruments, and the like. These advancements have provided, in part, for new medical imaging methods. One example method, whole-body imaging, can yield information on the vasculature of the entire body of a subject.

Compared to advances in the instruments used for X-ray imaging, advances in contrast-enhancing agents have not been as forthcoming. Current contrast-enhancing agents for medical imaging using X-rays can have limitations for applications such as whole-body imaging due to, among other things, rapid clearance from the body of a subject, greater than desired extravasation, renal toxicity and inability to target specific areas of the body of a subject.

BRIEF DESCRIPTION OF THE DRAWINGS

In the accompanying drawings, which are incorporated in and constitute a part of the specification, embodiments of contrast-enhancing agent formulations, pharmaceutical compositions containing the formulations, methods for making the formulations and methods for using the formulations in imaging are illustrated which, together with the detailed description given below, serve to describe the example embodiments of formulations, compositions, methods, and so on. It will be appreciated that the embodiments illustrated in the drawings are shown for the purpose of illustration and not for limitation. It will be appreciated that changes, modifications and deviations from the embodiments illustrated in the drawings can be made without departing from the spirit and scope of the invention, as disclosed below.

DETAILED DESCRIPTION

Definitions

Figure 1:
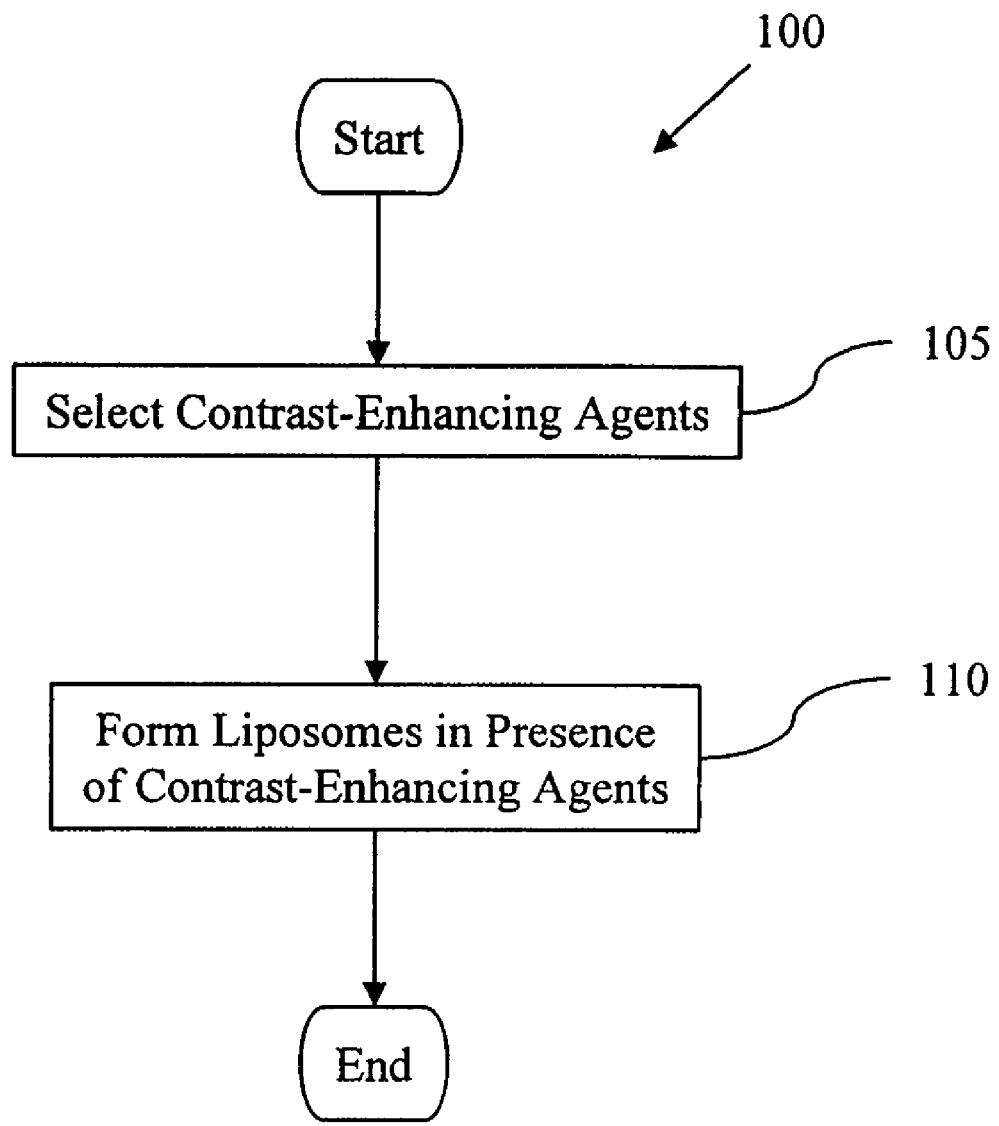
FIG. 1 illustrates an example method 100 of preparing liposomes containing or associated with contrast-enhancing agents.

Definitions of selected terms or phrases are contained immediately following, and throughout the disclosure. The definitions include examples of various embodiments and/or forms of components that fall within the scope of a term and that may be used for implementation. The examples are not intended to be limiting and other embodiments may be implemented. Both singular and plural forms of all terms fall within each meaning.

"X-ray imaging," as used herein, generally refers to any of a number of procedures using a source producing X-rays. Examples of X-ray imaging include computed tomography and the like.

"Computed tomography" or "CT", or "CAT," as used herein, generally refers to procedures using a rotating X-ray instrument or machine to produce X-ray radiation and direct it through areas of a subject as the instrument rotates. The radiation that is not absorbed by the subject generally is detected and recorded as data. Generally, the data are sent to a computer which creates detailed cross-sectional images, or slices, of organs and body parts based on differential absorption of X-rays by different areas of the subject. CT of high resolution may be called "micro CT."

"Whole body imaging," as used herein, generally refers to methodologies for obtaining images, using CT for example, of the entire body of a subject. In one type of whole body imaging, the entire vasculature system may be examined. Generally, imaging where the vasculature system is examined is called "blood pool imaging."

DESCRIPTION

This application describes example compositions comprising liposomes which contain or are associated with one or more contrast-enhancing agents. In one example, the liposomes contain or are associated with relatively high concentrations of contrast-enhancing agents. In one example, the liposomes contain one or more contrast-enhancing agents for X-ray imaging (e.g., CT imaging). In one example, the contrast-enhancing agents are not radioactive.

In one example, the liposomes have one or more hydrophilic polymers attached to or associated with the liposomes. In one example, the hydrophilic polymers are attached to or associated with the surface of the liposomes. When administered to a subject, the liposomes can provide increased contrast in the body of a subject. In one example, the increased contrast lasts for an extended period of time.

This application also describes example pharmaceutical compositions that contain the liposomes and contrast-enhancing agents, and example methods of making the compositions of liposomes containing contrast-enhancing agents. The application also describes example methods of using the compositions in X-ray imaging.

Contrast-Enhancing Agents

"Contrast-enhancing agent," as used herein, generally refers to a substance that affects the attenuation, or the loss of intensity or power, of radiation as it passes through and interacts with a medium. It will be appreciated that contrast-enhancing agents may increase or decrease the attenuation. Generally, the contrast-enhancing agents referred to herein may increase the attenuation of radiation. In one example, the contrast-enhancing agents described herein are contrast-enhancing agents for X-ray imaging. In one example, the contrast-enhancing agents can be used for CT. In one example, the contrast-enhancing agents used herein are nonradioactive. In one embodiment, the contrast-enhancing agents can contain iodine and may be called "iodinated.".

Contrast-enhancing agents may be classified in various ways. In one classification, for example, iodinated contrast-enhancing agents can be water soluble (e.g., monoiodinated pyridine derivatives, di-iodinated pyridine derivatives, tri-iodinated benzene ring compounds, and the like), water-insoluble (e.g., propyliodone and the like) or oily (e.g., iodine in poppy seed oil, ethyl esters of iodinated fatty acids of poppy seed oil containing iodine, and the like).

In one example, a grouping of iodinated contrast-enhancing agents are water soluble. Present water soluble iodinated contrast-enhancing agents can be derivatives of tri-iodinated benzoic acid. These compounds can have one or more benzene rings. These compounds can be ionic or nonionic. Suitable, nonionic compounds include, but are not limited to, metrizamide, iohexol, iopamidol, iopentol, iopromide, ioversol, iotrolan, iodoxanol and others.

Suitable ionic compound contrast-enhancing agents may be weakly acidic ($pK_a$ of from approximately 4.0 to 6.5) or weakly basic (pKa of from approximately 6.5 to 8.5). Generally, acids are capable of giving up or donating one or more protons. In their protonated form, the acids are generally substantially electrically neutral or uncharged. In their unprotonated form, the acids are generally substantially negatively charged. Suitable weakly acidic agents can have one or more carboxyl groups. The carboxyl groups are capable of donating a proton. The carboxyl groups may be attached to a benzene ring and/or may be part of a benzoic acid. Examples of such benzoic acids include, but are not limited to, acetrizoate, diatrizoate, iodamide, ioglicate, iothalamate, ioxithalamate, metrizoate, sodium meglumine ioxaglate and others.

Generally, bases are capable of accepting one or more protons. In their protonated form, the bases are generally substantially positively charged. In their unprotonated form, the bases are generally substantially neutral or uncharged. Suitable weakly basic agents may have one or more primary amine groups. The amines are capable of accepting a proton. The weakly basic agents may be amides.

Liposomes

"Liposomes," as used herein, generally refer to spherical or roughly spherical particles containing an internal cavity. The walls of liposomes can include a bilayer of lipids. These lipids can be phospholipids. Numerous lipids and/or phospholipids may be used to make liposomes. One example are amphipathic lipids having hydrophobic and polar head group moieties which may form spontaneously into bilayer vesicles in water, as exemplified by phospholipids, or which may be stably incorporated into lipid bilayers, with their hydrophobic moiety in contact with the interior, hydrophobic region of the bilayer membrane, and their polar head group moiety oriented toward the exterior, polar surface of the membrane.

As used herein, "phospholipids" include, but are not limited to, phosphatidic acid (PA), phosphatidylglycerol (PG), phosphatidylcholine (PC), egg phosphatidylcholine (EPC), lysophosphatidylcholine (LPC), phosphatidylethanolamine (PE), phosphatidylinositol (PI), phosphatidylserine (PS), and mixtures of two or more thereof. The vesicle-forming lipids of this type may be lipids having two hydrocarbon chains, typically acyl chains, and a polar head group. Included in this class are phospholipids, such as phosphatidylcholine (PC), phosphatidylethanolamine (PE), phosphatidic acid (PA), phosphatidylglycerol (PG), phosphatidylinositol (PI), and sphingomyelin (SM), plus others. These phospholipids can be fully saturated or partially saturated. They can be naturally occurring or synthetic. In another example, lipids that can be included in the liposomes can be glycolipids.

The phospholipids used in the example liposomes described herein can be those where the two hydrocarbon chains are between about 14 and about 24 carbon atoms in length, and have varying degrees of unsaturation. Some examples of these phospholipids are given below. Although the phospholipids listed below may be used, alone or in combination with other phospholipids, the list is not intended to be complete. Other phospholipids not listed herein can also be used.

Phospholipids
1-Myristoyl-2-Palmitoyl-sn-Glycero-3-Phosphocholine,
1-Myristoyl-2-Stearoyl-sn-Glycero-3-Phosphocholine,
1-Myristoyl-2-Palmitoyl-sn-Glycero-3-Phosphocholine,
1-Myristoyl-2-Stearoyl-sn-Glycero-3-Phosphocholine,
1-Palmitoyl-2-Oleoyl-sn-Glycero-3-Phosphate (POPA),
1-Palmitoyl-2-Oleoyl-sn-Glycero-3-Phosphocholine,
1-Palmitoyl-2-Oleoyl-sn-Glycero-3-Phosphoethanolamine (POPE),
1-Palmitoyl-2-Oleoyl-sn-Glycero-3-[Phospho-rac-(1-glycerol)] (POPG),
1-Palmitoyl-2-Oleoyl-sn-Glycero-3-[Phospho-L-Serine] (POPS),
1-Palmitoyl-2-Linoleoyl-sn-Glycero-3-Phosphate,
1-Palmitoyl-2-Linoleoyl-sn-Glycero-3-Phosphocholine, 1-Palmitoyl-2-Linoleoyl-sn-Glycero-3-Phosphoethanolamine,
1-Palmitoyl-2-Linoleoyl-sn-Glycero-3-[Phospho-rac-(1-glycerol)],
1-Palmitoyl-2-Linoleoyl-sn-Glycero-3-[Phospho-L-Serine],
1-Palmitoyl-2-Arachidonoyl-sn-Glycero-3-Phosphate,
1-Palmitoyl-2-Arachidonoyl-sn-Glycero-3-Phosphocholine,
1-Palmitoyl-2-Arachidonoyl-sn-Glycero-3-Phosphoethanolamine,
1-Palmitoyl-2-Arachidonoyl-sn-Glycero-3-[Phospho-rac-(1-glycerol)],
1-Palmitoyl-2-Arachidonoyl-sn-Glycero-3-[Phospho-L-Serine],
1-Palmitoyl-2-Docosahexaenoyl-sn-Glycero-3-Phosphate,
1-Palmitoyl-2-Docosahexaenoyl-sn-Glycero-3-Phosphocholine,
1-Palmitoyl-2-Docosahexaenoyl-sn-Glycero-3-Phosphoethanolamine,
1-Palmitoyl-2-Docosahexaenoyl-sn-Glycero-3-[Phospho-rac-(1-glycerol)],
1-Palmitoyl-2-Docosahexaenoyl-sn-Glycero-3-[Phospho-L-Serine],
1-Stearoyl-2-Myristoyl-sn-Glycero-3-Phosphocholine,
1-Stearoyl-2-Palmitoyl-sn-Glycero-3-Phosphocholine,
1-Stearoyl-2-Oleoyl-sn-Glycero-3-Phosphate,
1-Stearoyl-2-Oleoyl-sn-Glycero-3-Phosphocholine,
1-Stearoyl-2-Oleoyl-sn-Glycero-3-Phosphoethanolamine,
1-Stearoyl-2-Oleoyl-sn-Glycero-3-[Phospho-rac-(1-glycerol],
1-Stearoyl-2-Oleoyl-sn-Glycero-3-[Phospho-L-Serine],
1-Stearoyl-2-Linoleoyl-sn-Glycero-3-Phosphate,
1-Stearoyl-2-Linoleoyl-sn-Glycero-3-Phosphocholine,
1-Stearoyl-2-Linoleoyl-sn-Glycero-3-Phosphoethanolamine,
1-Stearoyl-2-Linoleoyl-sn-Glycero-3-[Phospho-rac-(1-glycerol)],
1-Stearoyl-2-Linoleoyl-sn-Glycero-3-[Phospho-L-Serine],
1-Stearoyl-2-Arachidonoyl-sn-Glycero-3-Phosphate,
1-Stearoyl-2-Linoleoyl-sn-Glycero-3-Phosphocholine,
1-Stearoyl-2-Arachidonoyl-sn-Glycero-3-Phosphoethanolamine,
1-Stearoyl-2-Arachidonoyl-sn-Glycero-3-[Phospho-rac-(1-glycerol)],
1-Stearoyl-2-Arachidonoyl-sn-Glycero-3-[Phospho-L-Serine],
1-Stearoyl-2-Docosahexaenoyl-sn-Glycero-3-Phosphate,
1-Stearoyl-2-Docosahexaenoyl-sn-Glycero-3-Phosphocholine,
1-Stearoyl-2-Docosahexaenoyl-sn-Glycero-3-Phosphoethanolamine,
1-Stearoyl-2-Docosahexaenoyl-sn-Glycero-3-[Phospho-rac-(1-glycerol)],
1-Stearoyl-2-Docosahexaenoyl-sn-Glycero-3-[Phospho-L-Serine],
1-Oleoyl-2-Myristoyl-sn-Glycero-3-Phosphocholine,
1-Oleoyl-2-Palmitoyl-sn-Glycero-3-Phosphocholine,
1-Oleoyl-2-Stearoyl-sn-Glycero-3-Phosphocholine,
1,2-Dimyristoyl-sn-Glycero-3-Phosphate (DMPA),
1,2-Dimyristoyl-sn-Glycero-3-Phosphocholine (DMPC),
1,2-Dimyristoyl-sn-Glycero-3-Phosphoethanolamine (DMPE),
1,2-Dimyristoyl-sn-Glycero-3-[Phospho-rac-(1-glycerol)] (DMPG),
1,2-Dimyristoyl-sn-Glycero-3-[Phospho-L-Serine] (DMPS),
1,2-Dipentadecanoyl-sn-Glycero-3-Phosphocholine,
1,2-Dipalmitoyl-sn-Glycero-3-Phosphate (DPPA),
1,2-Dipalmitoyl-sn-Glycero-3-Phosphocholine (DPPC),
1,2-Dipalmitoyl-sn-Glycero-3-Phosphoethanolamine (DPPE),
1,2-Dipalmitoyl-sn-Glycero-3-[Phospho-rac-(1-glycerol)] (DPPG),
1,2-Dipalmitoyl-sn-Glycero-3-[Phospho-L-Serine] (DPPS),
1,2-Diphytanoyl-sn-Glycero-3-Phosphate,
1,2-Diphytanoyl-sn-Glycero-3-Phosphocholine,
1,2-Diphytanoyl-sn-Glycero-3-Phosphoethanolamine,
1,2-Diphytanoyl-sn-Glycero-3-[Phospho-rac-(1-glycerol)],
1,2-Diphytanoyl-sn-Glycero-3-[Phospho-L-Serine],
1,2-Diheptadecanoyl-sn-Glycero-3-Phosphocholine,
1,2-Distearoyl-sn-Glycero-3-Phosphate (DSPA),
1,2-Distearoyl-sn-Glycero-3-Phosphocholine (DSPC),
1,2-Distearoyl-sn-Glycero-3-Phosphoethanolamine (DSPE),
1,2-Distearoyl-sn-Glycero-3-[Phospho-rac-(1-glycerol)] (DSPG),
1,2-Distearoyl-sn-Glycero-3-[Phospho-L-Serine],
1,2-Dibromostearoyl-sn-Glycero-3-Phosphocholine,
1,2-Dinonadecanoyl-sn-Glycero-3-Phosphocholine,
1,2-Diarachidoyl-sn-Glycero-3-Phosphocholine,
1,2-Diheneicosanoyl-sn-Glycero-3-Phosphocholine,
1,2-Dibehenoyl-sn-Glycero-3-Phosphocholine,
1,2-Ditricosanoyl-sn-Glycero-3-Phosphocholine,
1,2-Dilignoceroyl-sn-Glycero-3-Phosphocholine,
1,2-Dimyristoleoyl-sn-Glycero-3-Phosphocholine,
1,2-Dimyristelaidoyl-sn-Glycero-3-Phosphocholine,
1,2-Dipalmitoleoyl-sn-Glycero-3-Phosphocholine,
1,2-Dipalmitelaidoyl-sn-Glycero-3-Phosphocholine,
1,2-Dipalmitoleoyl-sn-Glycero-3-Phosphoethanolamine,
1,2-Dioleoyl-sn-Glycero-3-Phosphocholine (DOPC),
1,2-Dioleoyl-sn-Glycero-3-Phosphate (DOPA),
1,2-Dioleoyl-sn-Glycero-3-Phosphocholine (DOPC),
1,2-Dioleoyl-sn-Glycero-3-Phosphoethanolamine (DOPE),
1,2-Dioleoyl-sn-Glycero-3-[Phospho-rac-(1-glycerol)] (DOPG),
1,2-Dioleoyl-sn-Glycero-3-[Phospho-L-Serine] (DOPS),
1,2-Dielaidoyl-sn-Glycero-3-Phosphocholine,
1,2-Dielaidoyl-sn-Glycero-3-Phosphoethanolamine,
1,2-Dielaidoyl-sn-Glycero-3-[Phospho-rac-(1-glycerol)],
1,2-Dilinoleoyl-sn-Glycero-3-Phosphate,
1,2-Dilinoleoyl-sn-Glycero-3-Phosphocholine,
1,2-Dilinoleoyl-sn-Glycero-3-Phosphoethanolamine,
1,2-Dilinoleoyl-sn-Glycero-3-[Phospho-rac-(1-glycerol)],
1,2-Dilinoleoyl-sn-Glycero-3-[Phospho-L-Serine],
1,2-Dilinolenoyl-sn-Glycero-3-Phosphocholine,
1,2-Dilinolenoyl-sn-Glycero-3-Phosphoethanolamine,
1,2-Dilinolenoyl-sn-Glycero-3-[Phospho-rac-(1-glycerol)],
1,2-Dieicosenoyl-sn-Glycero-3-Phosphocholine,
1,2-Diarachidonoyl-sn-Glycero-3-Phosphate,
1,2-Diarachidonoyl-sn-Glycero-3-Phosphocholine,
1,2-Diarachidonoyl-sn-Glycero-3-Phosphoethanolamine,
1,2-Diarachidonoyl-sn-Glycero-3-[Phospho-rac-(1-glycerol)],
1,2-Diarachidonoyl-sn-Glycero-3-[Phospho-L-Serine],
1,2-Dierucoyl-sn-Glycero-3-Phosphocholine,
1,2-Didocosahexaenoyl-sn-Glycero-3-Phosphate,
1,2-Didocosahexaenoyl-sn-Glycero-3-Phosphocholine,
1,2-Didocosahexaenoyl-sn-Glycero-3-Phosphoethanolamine,
1,2-Docosahexaenoyl-sn-Glycero-3-[Phospho-rac-(1-glycerol)],
1,2-Didocosahexaenoyl-sn-Glycero-3-[Phospho-L-Serine], and
1,2-Dinervonoyl-sn-Glycero-3-Phosphocholine.

The liposome composition can be formulated to include amounts of fatty alcohols, fatty acids, and/or cholesterol esters or other pharmaceutically acceptable excipients. For example, the liposomes can include lipids that can stabilize a vesicle or liposome composed predominantly of phospholipids. For example, cholesterol between about 25 to 40 mole percent may be used.

In one embodiment, the type of liposomes used may be "sterically stabilized liposomes." Sterically stabilized liposomes can include a surface that contains or is coated with flexible water soluble (hydrophilic) polymer chains. These polymer chains may prevent interaction between the liposomes and blood plasma components, the plasma components playing a role in uptake of liposomes by cells of the blood and removal of the liposomes from the blood. Sterically stabilized liposomes may avoid uptake by the organs of the mononuclear phagocyte system, primarily the liver and spleen (reticulendothelial system or RES). Such sterically stabilized liposomes may also be called "long circulating liposomes."

Sterically stabilized liposomes can contain lipids or phospholipids that are derivatized with a polymer chain. The lipids or phospholipids that may be used generally may be any of those described above. One exemplary phospholipid is phosphatidylethanolamine (PE) with a reactive amino group which may be convenient for coupling to the activated polymers. An exemplary PE may be distearyl PE (DSPE).

Examples of polymers that are suitable for use in sterically stabilized liposomes include, but are not limited to, the hydrophilic polymers polyvinylpyrrolidone, polymethyloxazoline, polyethyloxazoline, polyhydroxypropyl methacrylamide, polymethacrylamide, polydimethylacrylamide, polylactic acid, polyglycolic acid, and derivatized celluloses, like hydroxymethylcellulose or hydroxyethylcellulose. Polylysine may be used. Lipid-polymer conjugates containing these polymers attached to a suitable lipid, such as PE, may be used. Other example polymers can be used.

In one embodiment, the polymer in the derivatized lipid or phospholipid can be polyethylene glycol (PEG). The PEG can have any of a variety of molecular weights. In one example, the PEG chain may have a molecular weight between about 1,000-10,000 daltons. Once a liposome is formed, the PEG chains may provide a surface coating of hydrophilic chains sufficient to extend the blood circulation time of the liposomes in the absence of such a coating. Such liposomes may be called "PEGylated liposomes." PEGylated liposomes can include so-called STEALTH® liposomes, provided by ALZA Corporation.

PEGylated liposomes may also include liposomes with PEG on their surface, where the PEG may be released from the liposome at some time after administration of the liposomes to a subject. In one example, there can be one or more bonds or linkages attaching the PEG, or other hydrophilic polymer, to the liposome surface and/or lipid molecules comprising the liposome surface. In one example, the bonds or linkages can be cleaved, providing for separation of the PEG from the liposome. For example, PEG may be attached to a lipid by one or more disulfide bonds. The disulfide bonds may be cleaved by free thiol, releasing the PEG from the liposome. Other types of cleavable links or bonds can be used to attach the polymers to the liposomes. Other types of agents or compounds can be used to cleave the bonds or linkages.

In one example, the liposomes used can have a composition of between about 60 and 75 mole % of one or more of the phospholipids with carbon chains between about 14-24 in length, as described above. A fraction of these phospholipids may be attached to one or more hydrophilic polymers such that between about 1 and 20 mole % of the liposome composition is phospholipid derivatized with polymer chains. In addition, the liposomes used may have between about 25 and 40 mole % cholesterol, or fatty alcohols, fatty acids, and/or other cholesterol esters or other pharmaceutically acceptable excipients, generally for the purpose of stabilizing the liposomes.

In another example, the liposomes can have a molecule or molecules, commonly called a "ligand," which may be accessible from the surface of the liposome, that may specifically bind or attach to, for example, one or more molecules or antigens. These ligands may direct or target the liposomes to a specific cell or tissue and may bind to a molecule or antigen on or associated with the cell or tissue. The ligand may be an antibody or antibody fragment. The antibody may be a monoclonal antibody or fragment. Such liposomes may be of a type called "targeted liposomes."

In one example, targeted liposomes can have lipids or phospholipids which have been modified for coupling antibody molecules to the liposome outer surface. These modified lipids may be of different types. The modified lipid may contain a spacer chain attached to the lipid. The spacer chain may be a hydrophilic polymer. The hydrophilic polymer may typically be end-functionalized for coupling antibody to its functionalized end. The functionalized end group may be a maleimide group, for selective coupling to antibody sulfhydryl groups. Other functionalized end groups may include bromoacetamide and disulfide groups for reaction with antibody sulfhydryl groups, activated ester and aldehyde groups for reaction with antibody amine groups. Hydrazide groups are reactive toward aldehydes, which may be generated on numerous biologically relevant compounds. Hydrazides may also be acylated by active esters or carbodiimide-activated carboxyl groups. Acyl azide groups reactive as acylating species may be easily obtained from hydrazides and permit the attachment of amino containing ligands.

In another example, the phospholipid can be modified by a biotin molecule. To attach the antibody molecule to the biotinylated liposome surface, once the liposome is formed, the antibody molecule may also be modified with biotin and then incubated in the presence of the avidin. Biotinylated lipids, such as biotinylated PE, may be commercially available.

In another example, lipids can be modified by a substrate for use in binding a targeting molecule to a liposome surface. Typically, substrates, as exemplified with biotin, may be relatively small, less than about 5,000 daltons for example, to allow their incorporation into multilamellar liposomes with a minimum of disruption of the lipid bilayer structures. The substrate may be one capable of binding irreversibly to a targeting molecule, to ensure that the targeting molecule remains bound to the liposomes over its lifetime in the bloodstream.

Preparation of Liposomes Containing Contrast-Enhancing Agents

Liposomes can be prepared by a variety of methods. Example methods include, but are not limited to, hydration of dried lipids, introduction of a volatile organic solution of lipids into an aqueous solution causing evaporation of the organic solution, and dialysis of an aqueous solution of lipids and detergents or surfactants to remove the detergents or surfactants, and other methods.

Liposomes can contain or may be associated with one or more contrast-enhancing agents. In one example, the liposomes may contain the contrast-enhancing agents. In the process of making liposomes, the contrast-enhancing agents may be added at any desired time. For example, contrast-enhancing agents may be associated with components of liposomes before liposomes are formed. Contrast-enhancing agents may be combined with liposome components at the time the liposomes are made. Contrast-enhancing agents may also be added after the liposomes are formed. Other methods of associating contrast-enhancing agents with liposomes may exist. Generally, contrast-enhancing agents which are hydrophilic in nature may be located or associated with the internal cavity of the liposome particles. Contrast-enhancing agents which are lipophilic in nature may be located or associated with the lipid bilayer of liposome particles. Generally, the contrast-enhancing agents herein are located or associated with the internal cavity of the liposome. The example liposomes contain at least 30 mg iodine/milliliter (I/ml) of liposome suspension when iodinated contrast enhancing agents are used. One example of the liposomes can contain between about 35 and about 250 mg I/ml of liposome suspension. One example of the liposomes can contain between about 37 and about 200 mg I/ml of liposome suspension. One example of the liposomes can contain between about 80 and about 160 mg I/ml of liposome suspension. One example of the liposomes can contain between about 100 and about 120 mg I/ml of liposome suspension. One example of the liposomes can contain between about 85 and about 100 mg I/ml of liposome suspension. One example of the liposomes can contain more than about 100 mg I/ml of liposome suspension.

There are a variety of methods for loading the contrast-enhancing agents into the liposomes. Example methods may be better appreciated with reference to the flow diagrams of FIGS. 1-3. While for purposes of simplicity of explanation, the illustrated methodologies are shown and described as a series of blocks, it is to be appreciated that the methodologies are not limited by the order of the blocks, as some blocks may occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks. While the figures illustrate various actions occurring in serial, it is to be appreciated that various actions could occur concurrently, substantially in parallel, and/or at substantially different points in time. The diagrams of FIGS. 1-3 are not intended to limit the implementation of the described examples.

Illustrated in FIG. 1 is an example method 100 for preparing liposomes containing or associated with contrast-enhancing agents. The method may include selecting one or more contrast-enhancing agents to be used (block 105). The method may also include forming liposomes in the presence of the one or more contrast-enhancing agents (block 110). Generally, the step illustrated as block 110 may be performed using the methods described earlier for preparing liposomes. These methods may include hydration of dried lipids, introduction of a volatile organic solution of lipids into an aqueous solution causing evaporation of the organic solution, dialysis of an aqueous solution of lipids and detergents or surfactants to remove the detergents or surfactants, and others.

Figure 2:
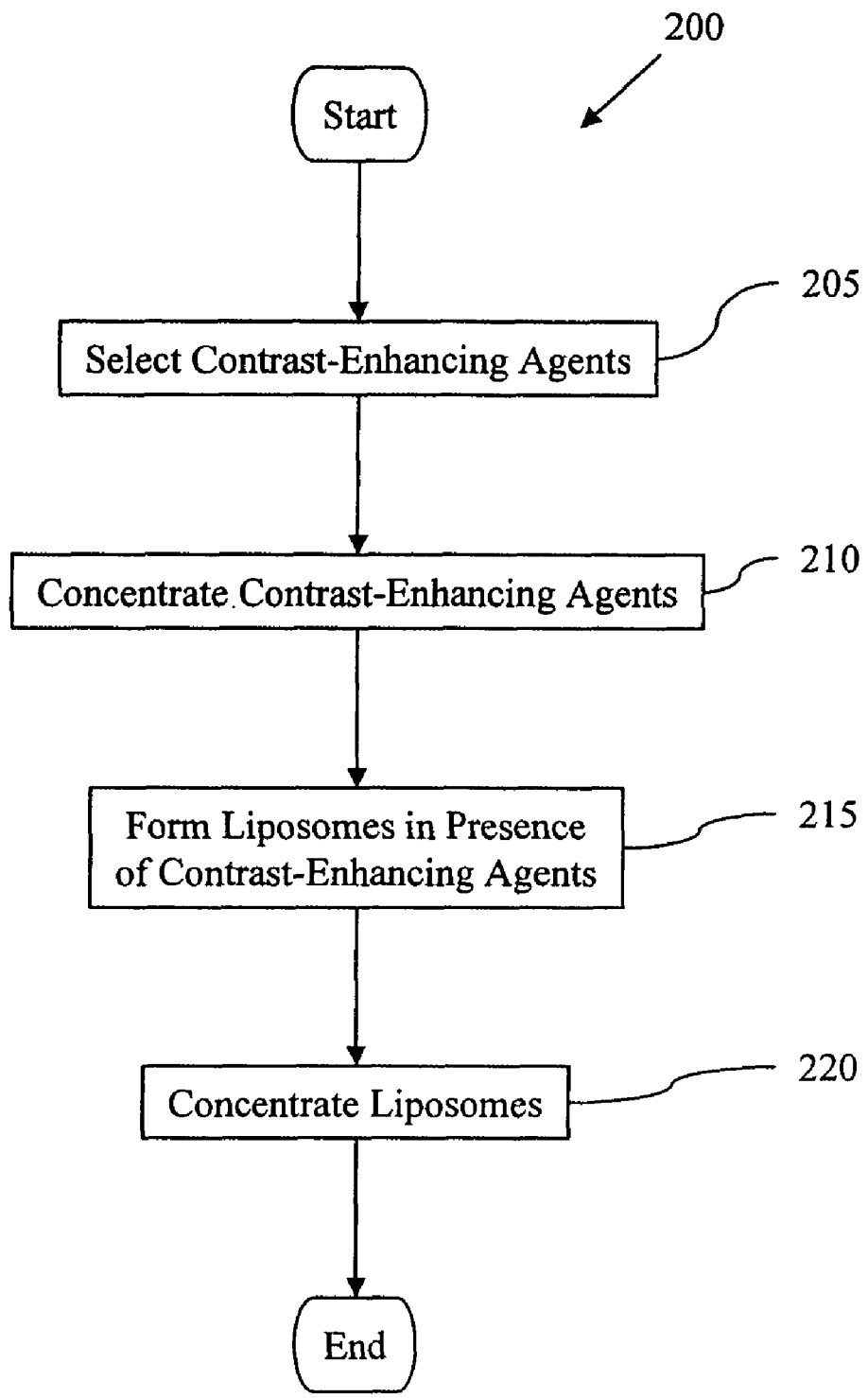
FIG. 2 illustrates another example method 200 of preparing liposomes containing or associated with contrast-enhancing agents.
Figure 3:
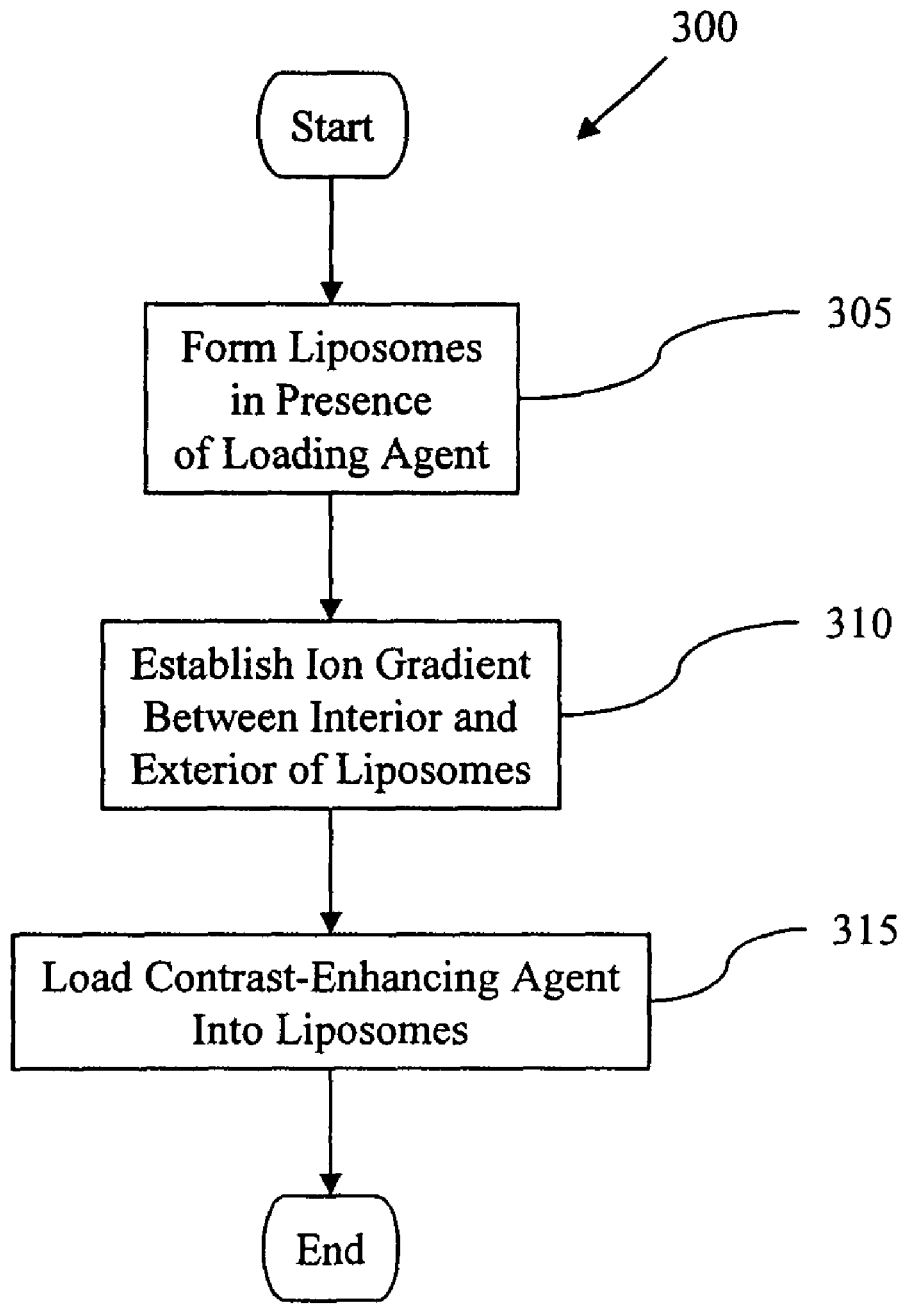
FIG. 3 illustrates another example method 300 of preparing liposomes containing or associated with contrast-enhancing agents.

Illustrated in FIG. 2 is another example method 200 for preparing liposomes containing or associated with contrast-enhancing agents. The method may include selecting one or more contrast-enhancing agents to be used (block 205). The method may also include concentrating the one or more contrast-enhancing agents (block 210). The method may also include forming liposomes in the presence of the one or more contrast-enhancing agents (block 215). The method may also include concentrating the liposomes (block 220).

Concentrating the one or more contrast-enhancing agents (block 210) can be performed using a variety of methods. In one example, a commercially available solution of one or more contrast-enhancing agents may be concentrated using the methods. In one example, the contrast-enhancing agents may be precipitated from a solution and the precipitated contrast-enhancing agents suspended in a liquid at a concentration higher than in the original solution. In another example, the contrast-enhancing agents in a solution may be concentrated by evaporation. One example of evaporation may be rotary evaporation. Other methods may be used. In one example, a solution of contrast-enhancing agents may be concentrated by at least 10%. In one example, a solution of contrast enhancing agents may be concentrated by 100% (i.e., 2-fold) or more. In another example, solid forms of the contrast enhancing agents may be dissolved in a liquid at a relatively high concentration (e.g., at a higher concentration than in commercially available solutions). In one example, heating may be used to increase the solubility of the contrast-enhancing agents in the solution. In another example, a solvent may be used in which the contrast-enhancing agents may be more soluble than in another solvent.

It will be appreciated that the viscosity of a liposome suspension generally is determined by the concentration of liposomes and generally is not determined by the viscosity of the liposome contents. For example, contrast-enhancing agents that have been encapsulated into liposomes may form a gel phase or even crystallize inside the liposomes (e.g., if the temperature is lowered). Generally, this may not affect the liposome suspension and may facilitate the stability of the liposome suspension (e.g., by reducing the probability of leakage of the contrast-enhancing agents from the liposomes).

After the liposomes are made and are in solution, the solution of liposomes may be concentrated to obtain a more concentrated solution of liposomes by decreasing the volume of the solution without substantially changing the number of liposomes in the solution. Concentrating the liposomes (block 220) can be performed using a variety of methods. When the liposomes are in an aqueous solution, concentration by removal of water may be called dewatering. One example method of dewatering can be diafiltration. In one example of diafiltration, a suspension of liposomes in a liquid may be passed through a filter or membrane to decrease the amount of liquid in which an amount of liposomes is suspended. Other example methods can include ion exchange, washing of the liposomes using ultracentrifugation, dialysis, and so on. These methods can result in example liposome suspensions with concentrations of between about 35-250 mg I/ml of liposome suspension. One example of the liposomes can contain between 37 and 200 mg I/ml of liposome suspension. One example of the liposomes can contain more than 100 mg I/ml of liposome suspension. These methods may also remove impurities from a suspension of liposomes. In one example, the impurities may include contrast-enhancing agents that have not been encapsulated into or associated with liposomes.

Illustrated in FIG. 3 is another example method 300 for preparing liposomes containing or associated with contrast-enhancing agents. The method 300 may include forming liposomes in the presence of a loading agent (block 305). The method may also include establishing an ion gradient between the interface and exterior of the liposomes (block 310). The method may also include loading one or more ionic iodinated benzenes into the liposomes (block 315).

The method illustrated in FIG. 3 may be of a type or class referred to as active or remote loading methods. In one example of active or remote loading, the contrast-enhancing agent or agents to be contained by or within the liposomes (e.g., contrast-enhancing agents) may enter liposomes after the liposomes have been formed or partially formed. Such formed liposomes generally are those whose process of making is completed. Partially formed liposomes may not have completed the making process.

In one example method, an ion gradient can be established from or between the outside of the liposome and the inside of the liposome (e.g., the concentration of one or more ions outside the liposomes is different than the concentration inside the liposomes) of the formed liposomes. The contrast-enhancing agent to be loaded into the liposomes can move from the outside of the liposomes to the inside of the liposomes. This movement may be due to movement of the contrast-enhancing agent through the membranes of the liposomes. Generally, contrast-enhancing agents capable of moving through membranes may be substantially neutral in electrical charge or uncharged. This movement may be based on a concentration gradient (e.g., a greater concentration of the contrast-enhancing agent outside the liposomes than inside the liposomes). This movement may be based on an ion gradient. This movement may be based on other factors or combinations of various factors. Once inside the liposomes, the different ion concentration inside the liposomes as compared to outside the liposomes may retard or prevent the contrast-enhancing agent from moving out of the liposomes. In one example, the different ion concentration inside the liposomes as compared to outside the liposomes can chemically alter the contrast-enhancing agent such that its movement out of the liposomes is retarded or prevented.

One example ion gradient can be a pH gradient. Hydrated liposomes may have a selected internal and external pH. This pH may have been selected based on the pH of the environment in which the liposomes were formed. The external solution in which the hydrated liposomes are present may then be titrated until a selected pH different from the internal pH is obtained. The external solution may also be exchanged with another solution of a selected pH different from the internal pH. For example, the original external solution in which the liposomes are present may have a pH of 5.5 and then be titrated or exchanged for a solution that may have a pH of 8.5. Once a contrast-enhancing agent enters into the liposomes, a contrast-enhancing agent inside the liposome may be chemically altered by accepting or donating one or more protons. A contrast-enhancing agent that has accepted or donated one or more protons may be charged. The charged contrast-enhancing agents may be unable or inhibited in their ability to pass through the liposome membrane. In these liposomes, the contrast-enhancing agents may be unable to exit or have a reduced ability to exit the liposomes.

In another example of active or remote loading, the formed or partially formed liposomes may contain a loading agent. For example, the liposomes may be formed in the presence of the loading agent. The loading agent may assist or facilitate entry of contrast-enhancing agents into the liposomes. The loading agent may facilitate establishing a certain condition inside the liposomes, such as a concentration of hydrogen ions for example. The loading agent may facilitate chemical alteration of a contrast-enhancing agent, such as facilitating the contrast-enhancing agent accepting or donating one or more protons. The loading agent may prevent or retard contrast-enhancing agents that enter the liposomes from leaving the liposomes.

In one example approach, a weakly acidic contrast-enhancing agent (pK$_a$ of from approximately 4.0 to 6.5) is loaded into liposomes. Such an agent may be weakly amphiphatic. The weakly acidic agent may be substantially uncharged in its protonated form. The weakly acidic agent may be substantially negatively charged in its unprotonated form. Generally, such weakly acidic agents may have one or more free carboxyl groups. Such free carboxyl groups may be ionizable in that they may donate a proton. Example weakly acidic contrast-enhancing agents may include acetrizoate, diatrizoate, iodamide, ioglicate, iothalamate, ioxithalamate, metrizoate, ioxaglate, and others In one example of this approach, liposomes can be formed in the presence of calcium acetate (e.g., $(CH_3COO)_2Ca$). The calcium acetate may be a loading agent. Calcium acetate is present inside the liposomes and in the external solution. The calcium acetate may then be removed from the phase exterior to the liposomes, by dilution for example. Calcium acetate inside the liposomes may dissociate into calcium ion and acetate ions. The acetate ions may combine with water inside the liposomes to yield acetic acid and hydroxide ion. Dilution of the solution external to the liposomes may cause acetic acid inside the liposomes to diffuse out of the liposomes, into the external solution, leaving hydroxide ions inside the liposomes. This may create a pH gradient in which the interior of the liposomes are more basic than the exterior of the liposomes. Addition of a weakly acidic contrast-enhancing agent to an exterior phase at a pH where a significant amount of the weakly acidic contrast-enhancing agent is protonated and uncharged may result in the contrast-enhancing agent moving into the interior of the liposomes. Such movement may be due to an outside-to-inside concentration gradient of the agent. Such movement may be due to forces favoring osmolar equilibrium as ammonia moves out of the liposomes. Such movement may be due to other or additional forces or combinations of such forces. When the contrast-enhancing agent moves to the interior of the liposomes, the contrast-enhancing agent may donate one or more protons, becoming negatively charged, and may be retarded or prevented from moving out of the liposome. Additions to, substitutions and variations of this approach may exist.

In one example approach, a weakly basic contrast-enhancing agent (pK$_a$ of from approximately 6.5 to 8.5) agent is loaded into liposomes. Such an agent may be weakly amphiphatic. The weakly basic agent generally is uncharged at or around neutral pH. The weakly basic agent may be substantially uncharged in its unprotonated form. The weakly basic agent may be substantially positively charged in its protonated form. Generally, such weakly basic agents may have one or more primary amine groups. Such primary amine groups may be ionizable in that they may accept a proton. Such weakly basic agents may be amides.

In one example of this approach, liposomes can be formed in the presence of ammonium sulfate $((NH_4)SO_4)$. The ammonium sulfate may be a loading agent. Ammonium sulfate is present inside the liposomes and in the external solution. The ammonium sulfate may then be removed from the phase exterior to the liposomes, by dilution for example. Ammonium sulfate inside the liposomes may dissociate into ammonium ions ($NH_4^+$) and sulfate ions ($SO_4^-$). Ammonium ions inside the liposomes may dissociate into ammonia and hydrogen ions. Dilution of the solution external to the liposomes may cause ammonia inside the liposomes to diffuse out of the liposomes, into the external solution, leaving hydrogen ions inside the liposomes. This may create a pH gradient in which the interior of the liposomes are more acidic than the exterior of the liposomes. Addition of a weakly basic contrast-enhancing agent to an exterior phase at a pH where a significant amount of the weakly basic contrast-enhancing agent is unprotonated and uncharged may result in the contrast-enhancing agent moving into the interior of the liposomes. Such movement may be due to an outside-to-inside concentration gradient of the contrast-enhancing agent. Such movement may be due to forces favoring osmolar equilibrium as ammonia moves out of the liposomes. Such movement may be due to other or additional forces or combinations of such forces. When the contrast-enhancing agent moves to the interior of the liposomes, the contrast-enhancing agent may accept one or more protons, becoming positively charged, and may be retarded or prevented from moving out of the liposome. Additions to, substitutions and variations of this approach may exist. A variety of other active or remote loading methods may also exist.

After liposomes are made, techniques for manipulating the liposomes can be used. For example, a preparation of liposomes made by standard techniques may vary in size and lamellarity (i.e., wall thickness) after it is made. Techniques like subjecting the liposomes to a high shearing force, extrusion of the liposomes through membranes, or sonication of the liposomes may be used either to select liposomes of a desired size or modify the liposomes so that they have a desired size. After manipulation of liposomes by these methods, the size distribution of the liposomes may be measured to ensure that liposomes of the desired size have been obtained. Techniques like as Fraunhofer diffraction and dynamic light scattering (DLS) may be used to measure the size distribution of the liposomes. These techniques generally measure an equivalent spherical diameter which, in the case of Fraunhofer diffraction, may be the diameter of a sphere with the same light scattering properties as the measured liposomes. In the case of DLS, equivalent spherical diameter may be the diameter of a sphere with the same diffusion coefficient as the measured liposomes. Generally, the example liposomes have an average diameter of 150 nm or less. Example preparations of liposomes may have an average diameter of approximately 120 nm or less. Example preparations of liposomes may have an average diameter of approximately 100 nm or less. It will be appreciated that other sizes can be used.

In one embodiment, a nano-scale liposomal formulation carrying over 30 mg of iohexol per ml of liposome is formulated using passive loading. In this formulation, the lipid composition of the bilayer is adjusted as described below to allow this amount of contrast-enhancing agent to be encapsulated. In one example, using pure DPPC (1,2-dipalmitoyl-sn-glycero-3-phosphatidylcholine) of C16 chain length, with about 40 mole % cholesterol and 5 mole % mPEG-DSPE (N-(carbonylmethoxypolyethyleneglycol 2000)-1,2-distearoyl-sn-glycero-3-phosphatidylethanolamine) (the polyethylene glycol-conjugated lipid that confers long circulating properties), the encapsulation of active molecules inside the liposomes is increased by 20% over what is possible using hydrogenated Soy PC (HSPC), a mixture of C16 and C18 lipids, or pure DSPC (1,2-distearoyl-sn-glycero-3-phosphocholine) of C18 chain length. Using a formulation of 55 mole % DPPC, 40 mole % cholesterol and 5 mole % mPEG-DSPE and an iohexol solution of 350 mg I/ml, an overall concentration of over 30 mg I/ml is achieved, with an average liposomal diameter of 100.6±3 nm, as determined by DLS.

In another embodiment, a liposomal formulation carrying over 80 mg of iohexol per ml of liposome is formulated using passive loading. In this formulation, an iohexol solution of 350 mg I/ml is concentrated to at least 400-450 mg I/ml and used to prepare liposomes as described in the previous paragraph. After the liposomes are obtained, the suspension of the liposomes is concentrated. Using this formulation, liposome suspensions with a concentration of over 85 mg I/ml are obtained.

Pharmaceutical Compositions and Administration to Subjects

The liposomes containing and/or associated with one or more contrast-enhancing agents can be part of a pharmaceutical composition suitable for administration to a subject. The compositions generally are administered using a route that delivers the composition to an area of interest. In one example, the compositions of contrast-enhancing agents are administered parenterally to the subject, such as through intravenous, intraarterial, subcutaneous, or other route of injection.

The formulation of the particular pharmaceutical composition generally will depend on the method by which the composition is administered to a patient. It will be appreciated that the pharmaceutical compositions can include salt, buffering agents, preservatives, other vehicles and, optionally, other agents. Compositions suitable for parenteral administration may comprise a sterile, pyrogen-free, aqueous or oleaginous preparation which is generally isotonic with the blood of the subject. This aqueous preparation may be formulated according to known methods using suitable dispersing or wetting agents and suspending agents. The sterile injectable preparation also may be a sterile injectable solution or suspension in a non-toxic parenterally-acceptable diluent or solvent. Among acceptable vehicles and solvents that may be employed are water, Ringer's solution, and isotonic sodium chloride or other salt, dextrose, phosphate buffered saline and the like, or combinations thereof.

The pharmaceutical compositions used may also contain stabilizers, preservatives, buffers, antioxidants, or other additives. In addition, sterile, fixed oils may be employed as a solvent or suspending medium. In addition, fatty acids such as oleic acid may be used in the preparation of injectables. Carrier formulations suitable for the administrations may be found in Remington's Pharmaceutical Sciences, Mack Publishing Co., Easton, Pa. The pharmaceutical compositions may conveniently be presented in unit dosage form.

Parenteral administration contemplates the use of a syringe, catheter or similar device, which delivers the pharmaceutical composition to a site. Delivery may result, at least initially, in the pharmaceutical composition being systemically distributed throughout the circulatory system of the subject.

Generally, the pharmaceutical compositions are administered to the subject at a point in time before the imaging of the subject is performed, although the compositions may also be administered during the imaging. The amount of the pharmaceutical compositions administered preferably results in increased contrast of one or more tissues of the subject. Ultimately, the attending physician or technician generally will decide the amount of pharmaceutical composition to administer to the subject. Generally, the increase in contrast can be any level above what is present without use of the contrast-enhancing agents in the pharmaceutical compositions. Example increases in contrast of at least about 50 HU, at least about 100 HU or more, to one or more organ systems, including the vasculature, may be obtained.

Applications

The compositions of liposomes containing contrast-enhancing agents or pharmaceutical compositions thereof, when administered to a subject, can maintain a level of contrast-enhancing agent in the blood and/or organs of a subject that results in an increased contrast and is detectable by X-ray imaging techniques. The increase in contrast may be detectable for an extended period of time. Depending on the particular application, the compositions described herein may have half lives in the circulation of from minutes to hours, to even days. In one example, half lives in the circulation of from 8 to 24 hours may be obtained. In one example, an administered composition provides an enhanced contrast that may remain detectable at least 30 minutes after administration. In another example, an administered composition provides an enhanced contrast that may remain detectable at least 5 minutes after administration. Many applications, including those in anatomic, functional and molecular imaging may be possible. For example, use of the compositions described herein may have applications in cardiology, oncology, neurology and other areas.

In one embodiment, blood pool imaging can be used to detect and, in some cases, quantify ischemia. For example, because injection of the pharmaceutical compositions generally alters the contrast of the entire vasculature, reduced blood flow as is present in ischemia may be detected. A variety of types of ischemia may be detected, including that causing ischemia bowel disease, pulmonary embolism, and types of ischemia that produce cardiomyopathy, and others. In other applications, aneurysms may also be detected.

In one embodiment, the compositions described herein can be used in cardiac imaging to detect, examine and/or assess stenosis, and the therapy or remediation of stenosis, as occurs in angioplasty, for example. The utility of such techniques may be enhanced through the use of contrast-enhancing agent preparations, such as those described herein.

In one embodiment, the compositions described herein can be used to detect myocardial microcirculatory insufficiencies. Myocardial microcirculation is known to display signs of obstruction before the epicardial arteries show signs of obstruction. Therefore, detection of obstruction in the myocardial microcirculation may be an earlier detector of atherosclerosis in presymptomatic, at-risk patients, than conventional methods. The compositions described herein may facilitate detection of obstructions in the myocardial microcirculation.

In another embodiment, the compositions described herein can be used to detect and characterize a wide range of tumors and cancers. These applications may be facilitated by the property of sterically stabilized liposomes being present for extended periods of time in the circulation and to extravasate at regions where the vasculature is "leaky," such as in tumors, for example. The leakiness of the vasculature in tumors may be attributed to the high proportion of neovasculature, the result of continuing angiogenesis as the tumor grows in size. Upon encountering such leaky vasculature, liposomes may leave the circulation, driven with the extravasate fluid, by hydrostatic pressure. Such liposomes generally do not return to the circulation after extravasation since the pressure gradient opposes such return. Such methods may be used to detect both primary and metastatic tumors.

In other embodiments, the compositions can be used for "staging" and/or classification of tumors. These applications may depend on, among other things, differences in the "leakiness" of the vasculature of a given tumor or cancer at different stages of progression.

In one embodiment, the compositions can be used in the area of monitoring and characterizing injury and healing of damaged spinal cords. In a typical spinal cord injury, as occurs in an automobile accident for example, there may also be damage to tissue surrounding the spinal cord. It is thought that the process of healing of the surrounding tissue may be deleterious to healing of the spinal cord. It is thought that formation of neovasculature in the surrounding tissue, as occurs in healing of the surrounding tissue, may inhibit healing of the spinal cord. It is thought that by inhibiting healing of the surrounding tissue, and the formation of neovasculature in the surrounding tissue, the spinal cord may heal. Subsequently, the surrounding tissue may heal. The compositions of contrast-enhancing agents described here may be useful for monitoring the healing and inhibition of healing of the tissue surrounding the spinal cord.

There may be a variety of other applications for the compositions described herein. For example, the compositions may be used in detection and monitoring of inflammation, reperfusion injuries, and the like.

Additionally, the liposomes which comprise the compositions of contrast-enhancing agents can be targeted to desired cells and tissues in the body of a subject by, for example, attaching antibodies to the surface of the liposomes. This targeting may result in enhanced contrast to the targeted areas of the body.

The compositions of contrast-enhancing agents may have a relatively long residence time in the body, low extravasation, except in those areas of the vasculature that are leaky as described above, may be relatively nontoxic to the kidneys and may be used to target specific areas of the body. Additionally, the traditional osmolality related toxicity problems associated with ionic contrast-enhancing media generally are not an issue with the liposomal encapsulates since the high osmolality phase is interior to the liposomes and generally is not exposed to the blood.

EXAMPLES

Example 1

Preparation of PEGylated Liposomes Containing Iohexol

Example liposomal iohexol formulations can be produced as follows. Briefly, a lipid mixture (200 mM) of 1,2-Dipalmitoly-sn-glycero-3-phosphocholine (DPPC), cholesterol (chol) and N-(carbonyl-methoxypolyethyleneglycol 2000)-1,2-distearoyl-sn-glycero-3-phosphoethanolamine (DSPE-MPEG2000), in a 55:40:5 molar ratio, was dissolved in ethanol at 65° C. The ethanol solution was then hydrated with iohexol (350 mg I/ml) for 1.5-2 hours. Liposomes were extruded on a 10 ml Lipex Thermoline extruder (Northern Lipids, Vancouver, British Columbia, Canada) with 5 passes through a 0.2 µm Nucleopore membrane (Waterman Inc., Newton Mass.) and 7 passes through a 0.1 µm Nucleopore membrane (Waterman Inc., Newton Mass.). Liposomes were then be dialyzed in a 300,000 molecular weight cutoff (MWCO) dialysis bag against phosphate buffer saline (PBS) overnight to remove the free iohexol.

The size of the resulting example liposomal iohexol formulations can be determined by dynamic light scattering (DLS) using a modified BI-90 goniometer, a JDS uniphase 532 nm laser, Hamamastu photomultiplier and Brookhaven DLS Software Version 3.16. The average diameter of the liposomal iohexol capsules was 100.6 nm (STD=3.0 nm), which is in nano-scale range, as determined by DLS.

The iohexol concentrations of example liposomal iohexol formulations can be determined by measuring the absorption at 245 nm using a UV-Vis spectrophotometer. Equivalent iodine concentrations can then be calculated. In the example preparations, different lipid hydration times (1.5 hours and 2 hours) resulted in different iohexol loading concentrations (30 and 34.8 mg I/ml respectively). The 30 mg I/ml iohexol liposomal formulation was used in the in vitro stability tests described below, and the 34.8 mg I/ml iohexol liposomal formulation were used in the in vivo CT imaging experiment described below.

The osmolarity of liposomal iohexol formulation can be measured by, for example, Vapro® vapor pressure osmometer (Wescor Inc.). The osmolarity of the example iohexol formulations ranged between 305 to 315 mmol/kg.

Example 2

In Vitro Stability of PEGylated Liposomes Containing Iohexol

The in vitro stability of example liposomal iohexol formulations can be determined by measuring the leakage of iohexol from liposomal iohexol formulations both in PBS at 4° C. and in plasma at 37° C. In the procedure, 1 ml of an example liposomal iohexol formulation was placed in a 300,000 MWCO dialysis bag and dialyzed against 250 ml PBS at 4° C. At each time point (0, 1, 2, 3, 8, 24 hours, and 3, 4, 5, 6, 8, 10, 18 days), 1 ml of the dialysate was removed for a UV absorption-based iohexol measurement. At least three data points were obtained at each time point. After measurement, samples were returned to the PBS to maintain constant volume.

To measure stability in plasma, the example liposomal iohexol formulations can be dialyzed against 250 ml PBS at 25° C. for 1 hour to remove the free iohexol. In these experiments, 1 ml liposomal iohexol formulations was placed in a 300,000 MWCO dialysis bag with 4 ml of human plasma, and dialyzed against 250 ml PBS at 37° C. (1:4 ratio was chosen). One ml of the external phase was removed at 0, 1, 2, 3, 4, 5, 6 and 8 hours respectively, and analyzed by the UV-vis absorption. Since plasma components also leak from the dialysis bag and have a finite absorbance at 245 nm, a control experiment, where a PBS-plasma mixture is dialyzed against PBS, was also performed. The absorbance of the external phase was subtracted from that for the liposomal iohexol formulation experiments and the resulting absorbance traces can be representative of the leakage of iohexol from liposomal iohexol formulations. The results showed that the liposomal iohexol formulation was stable in PBS and in human plasma.

Figure 4:
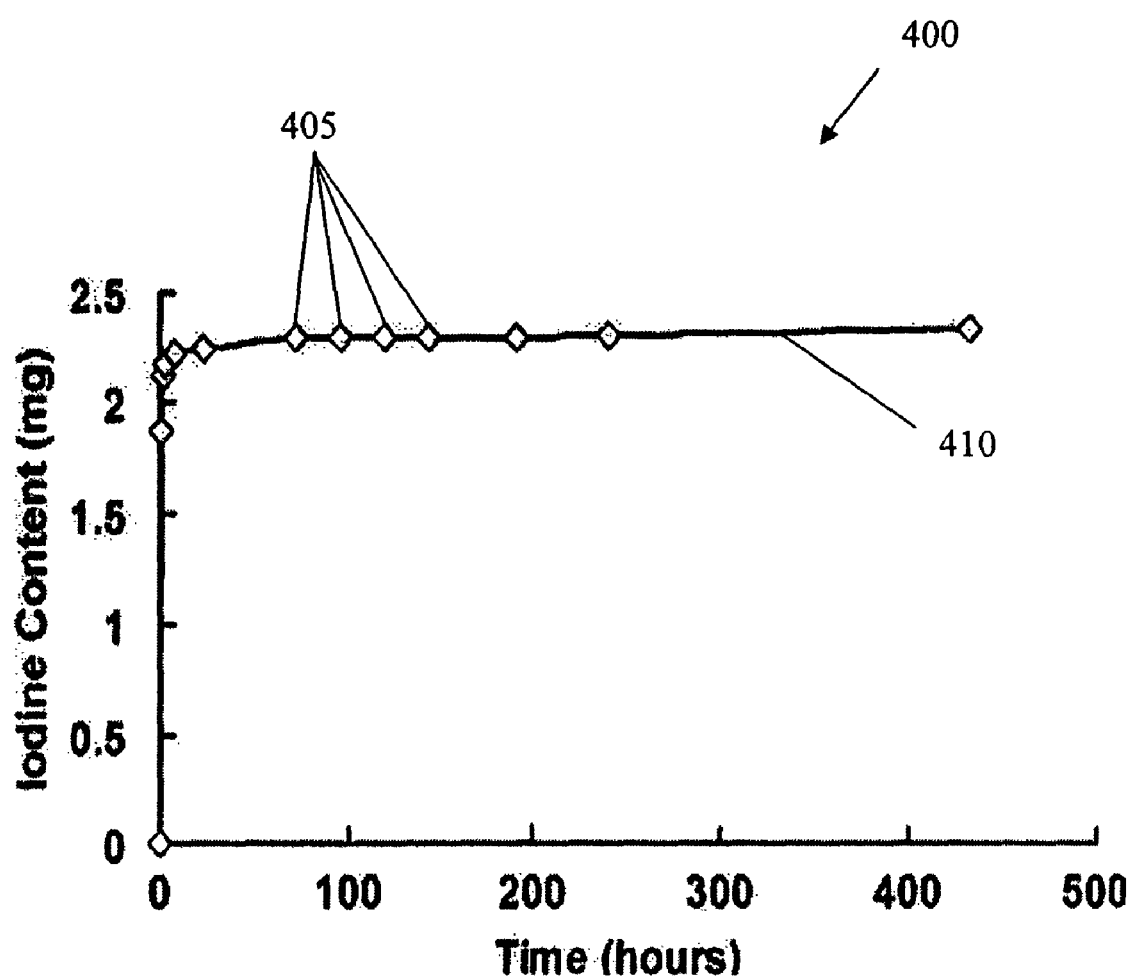
FIG. 4 shows example results 400 from an in vitro stability test of one embodiment of a liposomal iohexol formulation when dialyzed with PBS at 4° C. The total iodine amount is 30 mg iodine.

The example leakage curves 400 of iohexol is shown in FIG. 4. The example liposomal iohexol formulation (30 mg I/ml) was dialyzed against 250 ml of PBS at 4° C. At example time points 405 of 0, 1, 2, 3, 8, 24 hours, and 3, 4, 5, 6, 8, 10 and 18 days, the dialysate was tested for the amount of iohexol. The example leakage curve 410 was obtained by drawing a line through the data at each time point. The data show that the curve stabilized after 1 hour of dialysis. Liposomal iohexol exhibited a leakage of 7.4% of the total encapsulated iohexol over 8 hours, and 7.8% for 18 days by equilibrium dialysis at 4° C. The shelf life of liposomal iohexol formulation therefore can be longer than 18 days.

Figure 5:
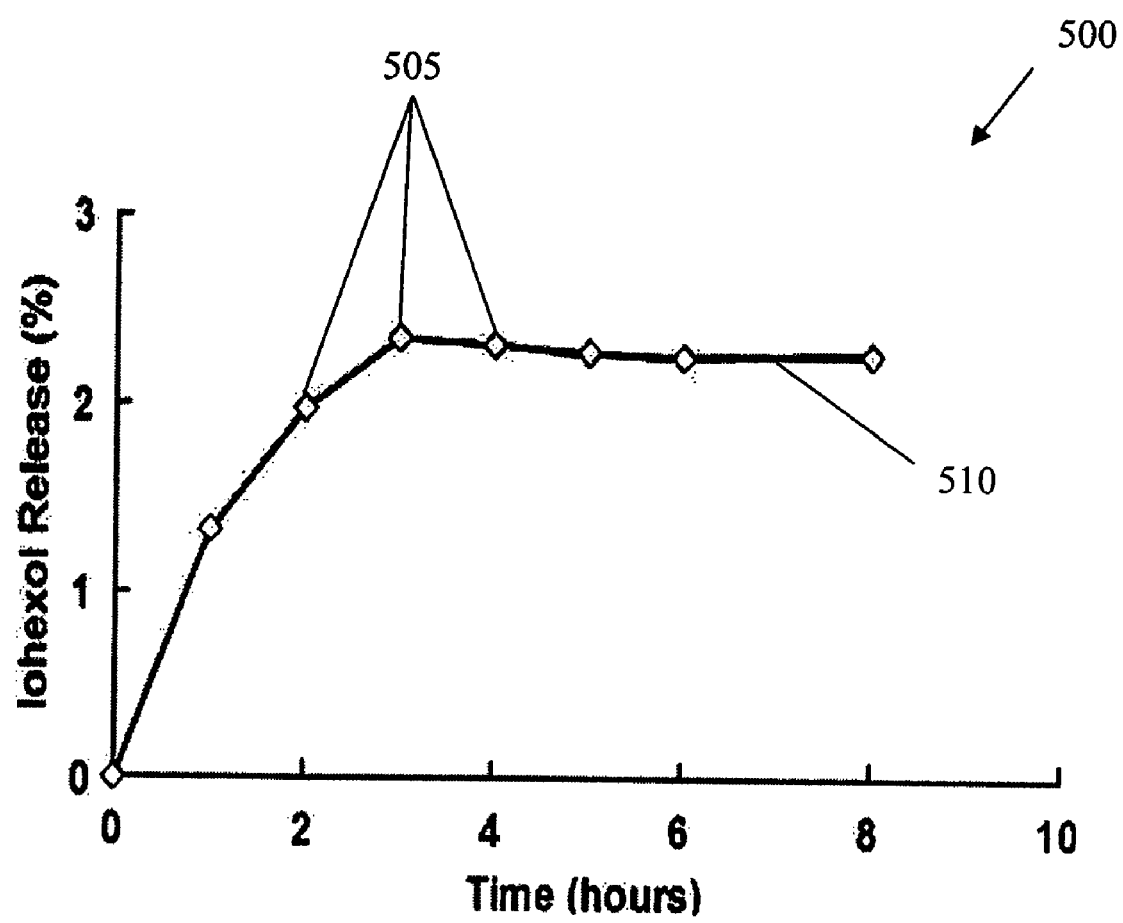
FIG. 5 shows example results 500 from an in vitro plasma stability test of one embodiment of a liposomal iohexol formulation when dialyzed against PBS at 37° C. The total iodine content is 28 mg iodine.

The leakage curves 500 of an example iohexol-plasma mixture is shown in FIG. 5. Liposomal iohexol that had previously been dialyzed against PBS for 1 hour was used in this study to determine the contribution of plasma to leakage of iohexol from the liposomes. At example time points 505 of 0, 1, 2, 3, 8, 24 hours, and 3, 4, 5, 6, 8, 10 and 18 days, the dialysate was tested for the amount of iohexol. The example leakage curve 510 was obtained by drawing a line through the data at each time point. The data show that the curve stabilized after 3 hours, and the liposomal iohexol formulation exhibited a leakage of 2.3% of the total encapsulated iohexol for the 8 hour period, beyond the leakage observed during storage in PBS. Together, these results indicate that the liposomal iohexol formulation can be about 90% encapsulated when stored for 18 days and then injected.

Example 3

In Vivo Studies Using Imaging of PEGylated Liposomes Containing Iohexol in a Rabbit A female rabbit weighing 2.2 kg was anesthetized with 35 mg/kg ketamine and 5 mg/kg xylazine given intramuscularly, followed by 2% isoflurane vapor given by face cone. After tracheal intubation and placement of venous catheter in an ear vein, 20 mg pentobarbital was given intravenously. The animal's lungs were ventilated using a pressure control ventilator set to peak airway pressure of 15 cm $H_2O$, and 25 breaths $min^{-1}$. After transport to the CT scanner, the animal was given 0.25 mg of pancuronium (muscle relaxant) to insure minimal motion during the image acquisition. Supplemental pentobarbital was given every 30-60 minutes, 10-20 mg per dose. An initial volume image of the chest and abdomen was obtained using a 4 slice Phillips MX8000 MDCT scanner in spiral scanning mode, (100 mAs, 120 keV) with a single slice equivalent pitch of 1.25, and a slice collimation and thickness of 1.3 mm. Images were reconstructed into a 512×512 matrix using a standard reconstruction kernel (the "B" kernel). A 0.5 second gantry rotation speed was used. During each imaging protocol, the rabbit was held apneic with airway pressure fixed at 20 cm $H_2O$ (e.g. near total lung capacity) using an underwater bubbler tube on the exhalation port. Next, 15 ml of 34 mg I/ml liposomal iohexol formulation was hand-injected followed by a repeat volume image, then a second injection of 15 ml of liposomal iohexol formulation suspension was followed by a third volume image. A total dose of 475 mg iodine per kg was given in the two injections. Repeat volume images were then initiated at approximately 12, 60, 90, 120, 150 and 180 minutes after the second contrast injection. Following the last image acquisition (~3.5 hr post injection of contrast agent), the animal was euthanized with an overdose of pentobarbital and a final, high resolution image was obtained with no motion artifact (with the same airway pressure and image acquisition settings). Finally, an ultrahigh resolution scan was obtained using an ultra sharp reconstruction kernal ("D" kernal and a 1024×1024 image matrix) to evaluate anatomic detail without the presence of cardiogenic motion.

Example 4

Image Reconstitution

Subsequent offline example reconstructions were performed for each of the scans obtained as described in Example 3 with the smallest field of view (5 cm×5 cm, 0.1 mm voxel size) for 3D viewing of the heart. The enhanced heart chambers were visualized by selecting appropriate settings of the volume rendering software present on the Philips MXV workstation software (version 4.1). Once the settings were established, the same rendering and display settings were used for all time points. Additional structures were segmented at various time points.

Quantitative analysis was performed by locating regions of interest (ROI) in the aorta, heart, kidney (core and cortex), liver, muscle and spleen. Mean Hounsfield units (HU) were determined at each time point to enable tracking of any decay in contrast concentration with time in each of these structures. Slice and slice location of the ROI's were adjusted for minor variations in anatomic configuration of the rabbit from time point to time point.

Example 5

Time-Attenuation of PEGylated Liposomes Containing Iohexol In Vivo

Figure 6:
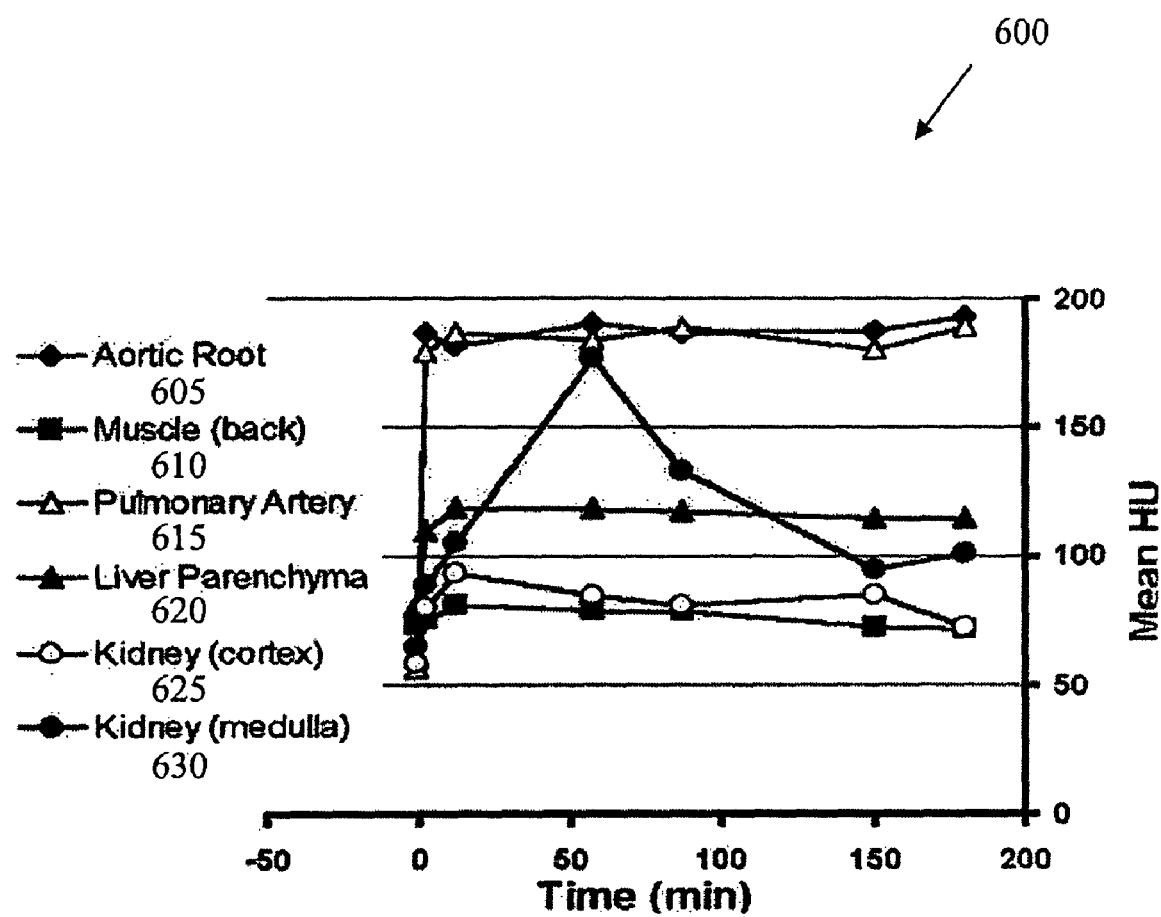
FIG. 6 shows example time-attenuation curves 600 of various regions of interest at different post-injection times after intravenous administration of one embodiment of a liposomal iohexol formulation (injection to 2.2 kg rabbit vein at a dose of 475 mg I/kg) given in two incremental injections.
Figure 7:
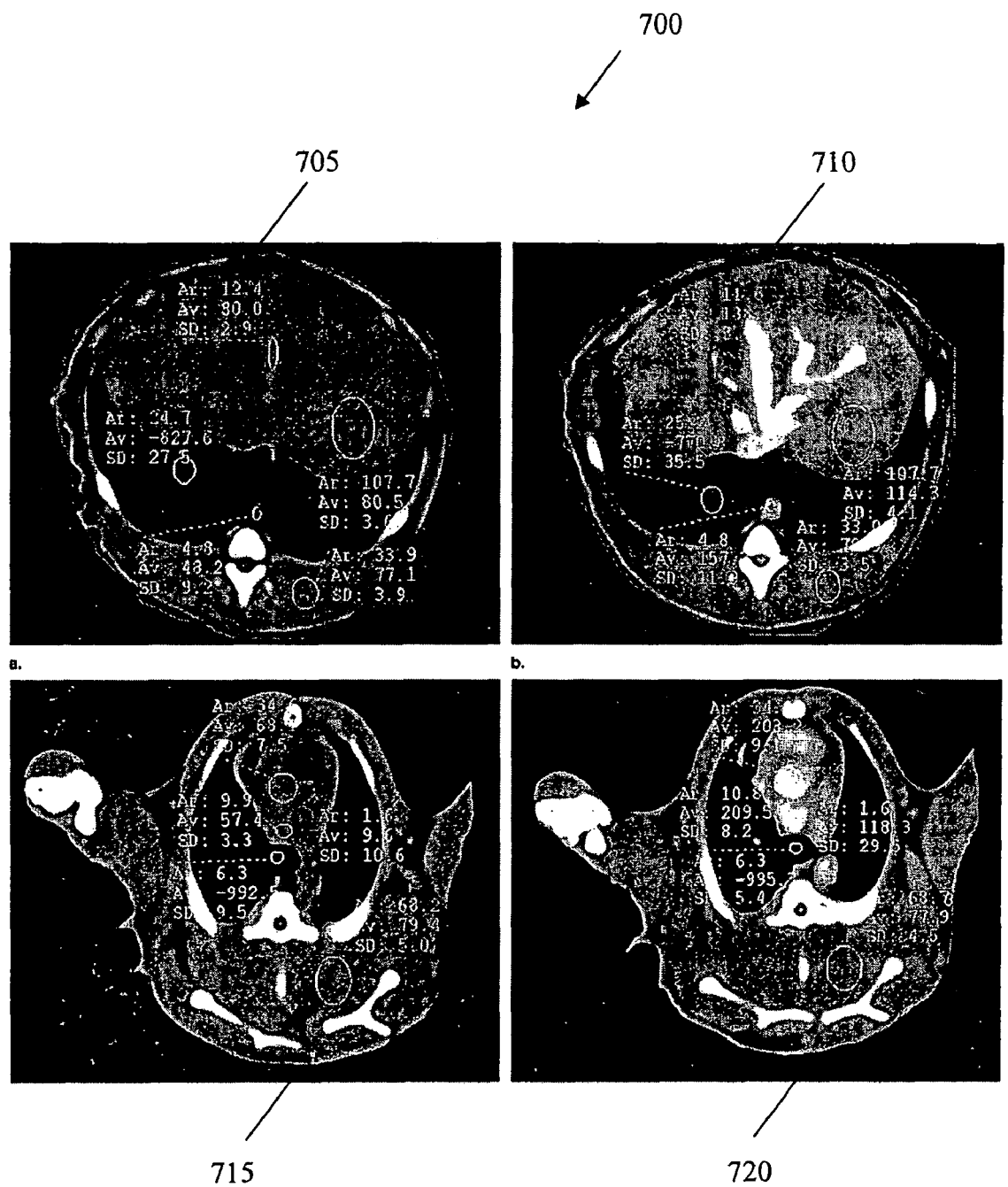
FIG. 7 shows example pre- and post-enhancement computed tomography (CT) images 700 of one embodiment of liposomal iohexol: 2.2 kg rabbit with 34.8 mg/ml iodine IV injection. Left Panels 705, 715 (FIG. 7a): pre-contrast; Right Panels 710, 720 (FIG. 7b): 2 hours 18 minutes post injection. Upper panels 705, 710 are images taken at the level of the liver. Lower panels 715, 720 are images taken at mid heart level.

The example image analysis described in Example 4 was performed at regions of interest in the aorta, kidney (medulla and cortex), liver parenchyma, back muscle, left main coronary artery, pulmonary artery, and in the main stem bronchus (as a control value) and plotted over time in a graph 600 (FIG. 6). Mean attenuations (Hounsfield units) were determined at the time points stated in Example 3 to quantify the decay in contrast with time in each of these locations. The data show the enhancement and maintenance of contrast over time in various regions of interest. The average attenuation in the aorta 605, pulmonary artery 615 and liver cortex 3.5 hours post contrast injection attenuation was 200 HU (enhancement 130 HU), and in the kidney cortex 625 the attenuation was 75 HU (enhancement 25 HU). Attenuation in the blood pool rose rapidly post-injection, and remained virtually constant for the 3.5 hours of study. A slight increase in attenuation in the liver parenchyma 620 was observed. A transient increase in the kidney core 630 was observed, indicating early clearance with little to no clearance later in the study. The small region of interest placed over the left main coronary artery indicated attenuation of 9 HU at base line and peaked at a value of 118 HU. FIG. 7 shows 0 hour baseline 705 and peak enhanced 710 images obtained 2 hours 18 minutes post liposomal injection at the level of the liver. FIG. 7 also shows 0 hour baseline 715 and peak enhanced 720 images obtained 2 hours 18 minutes post liposomal injection at the level of the mid-heart.

These data indicate the residence time of example PEGylated liposome formulations, which provided contrast enhancement, to be more than 3 hours. Additionally, the data show that contrast enhancement in muscle can be low, indicating the liposomal iohexol can be retained in the blood vessels and does not rapidly extravasate. Additionally, the contrast enhancement in the liver parenchyma indicated that clearance of the composition may substantially be due to the liver, and not the kidneys.

Example 6

Figure 8:
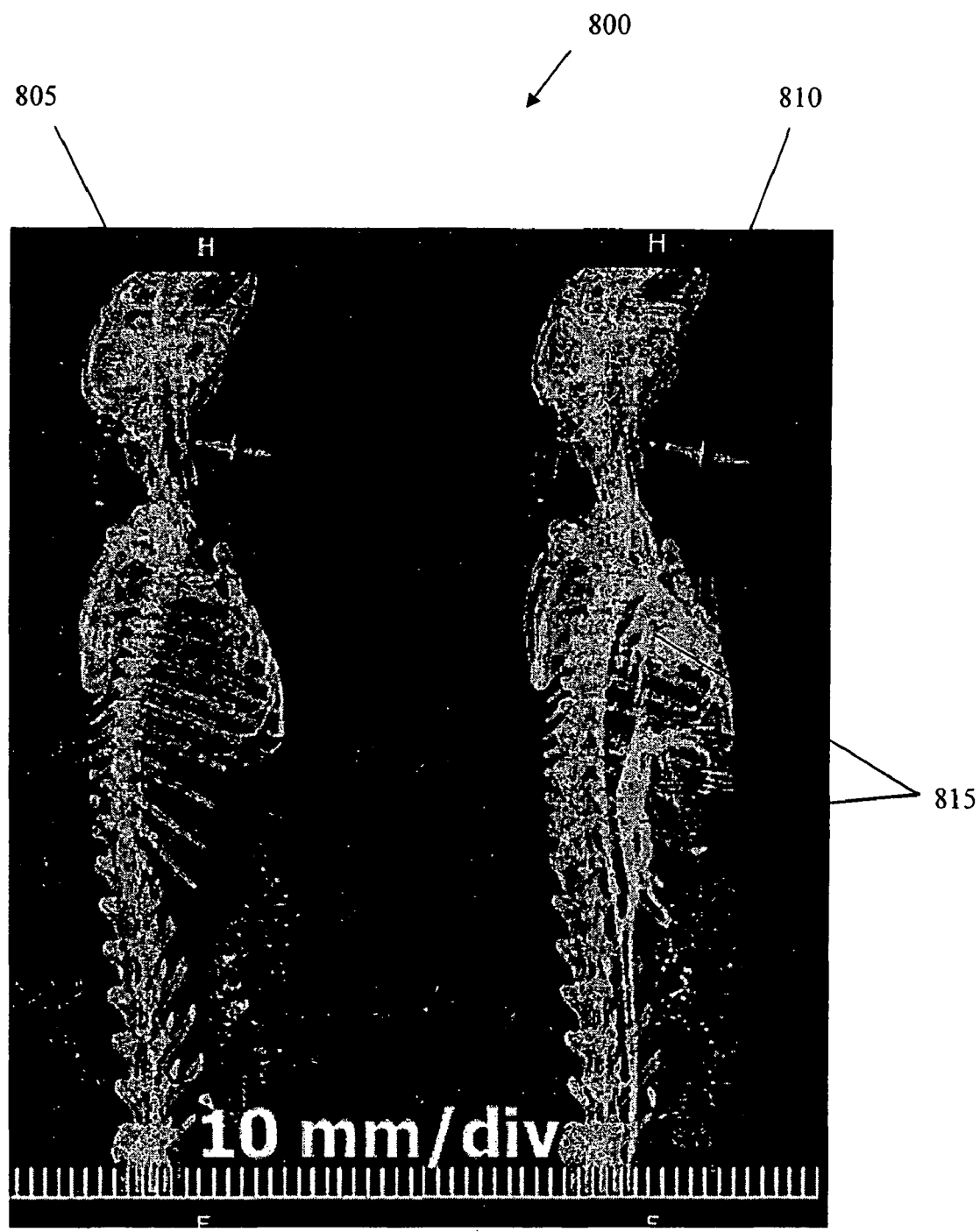
FIG. 8 shows example volume-rendered CT images 800 of a rabbit torso. Left panel 805: right lateral view before contrast injection; Right panel 810: right lateral view 2 hours 18 minutes after injection of 475 mg I/kg of one embodiment of a liposomal iohexol formulation. Note the enhanced vascular bed seen in the right panel 815.

In Vivo Images of Heart After Administration of PEGylated Liposomes Containing Iohexol Additionally, example images 800 (FIG. 8), 900 (FIG. 9), 1000 (FIG. 10) and 1100 (FIG. 11) of the rabbit heart were analyzed. FIG. 8 shows volume rendered images 800 of the whole rabbit, before 805 and 2 hours 18 minutes after injection of the liposomal iohexol formulation 810. Enhancement to the vasculature 815 due to the liposomes can be seen. The results show that, even more than 2 hours after injection, the blood vessels can be visible 815 while, using the same display and rendering parameters, they may not be visible before liposome administration. This enhancement can persist up until the time that the animal is euthanized at more than 3 hours after injection of the second dose of liposomes.

Figure 9:
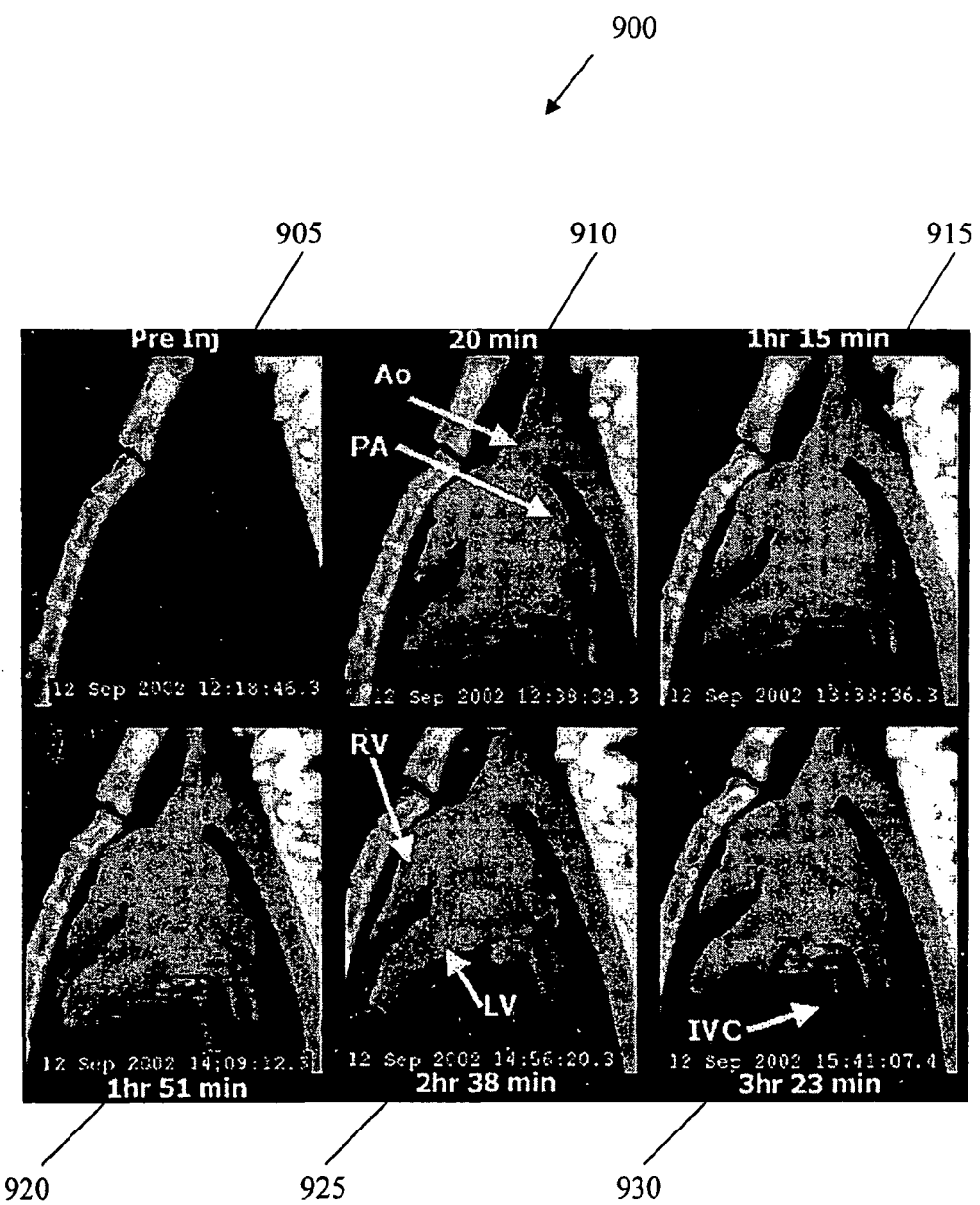
FIG. 9 shows example volume-rendered CT images 900 of an in vivo rabbit heart imaged before 905 and at multiple time sequences post injection 910, 915, 920, 925, 930 of one embodiment of liposomal iohexol. All volume-rendering parameters and display parameters were held constant across time points.

FIG. 9 shows volume images 900 of the rabbit heart acquired pre-contrast 905 and at 20 minutes 910, 1 hour 15 minutes 915, 1 hour 51 minutes 920, 2 hour 38 minutes 925, and 3 hour 23 minutes 930 after administration of the liposomal iohexol formulation. All display and rendering parameters are identical for all images. The anatomies of all four heart chambers can be distinctly visualized along with the associated great vessels. Note that there may be absence of blood pool in the upper left panel 905 and the persistent enhanced opacity of the blood pool up to the final panel representing 3 hours 23 minutes post injection 930. Visible structures include: right ventricle 935 (RV); left ventricle 940 (LV); Aorta 945 (Ao); pulmonary artery 950 (PA); and the inferior vena cava 855 (IVC). These images demonstrated sustained contrast even 3 hours after administration of the liposomal iohexol.

Figure 10:
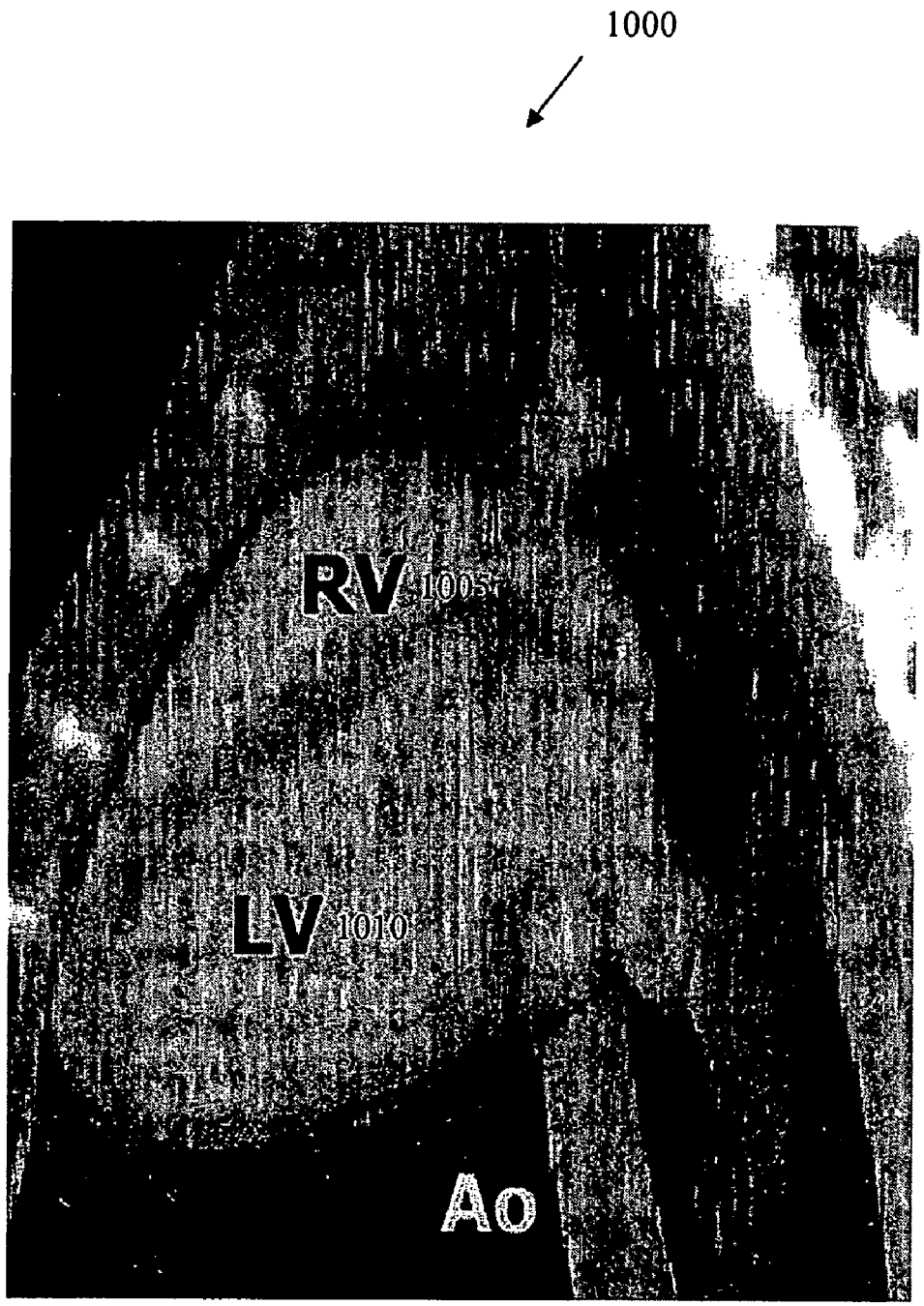
FIG. 10 shows an example of a thick-slab rendering 1000 of ultra-high resolution CT scan (24 line pair per cm) of post-mortem rabbit (no cardiac motion). Rabbit was sacrificed 3.5 hours after the second injection of one embodiment of liposomal iohexol. Images were reconstructed to fit a 1,024×1,024 matrix with a 0.5-cm field of view.

FIG. 10 shows a thick-slab rendering 1000 of the heart obtained at ultrahigh resolution after the rabbit was euthanized and thus cardiac motion was eliminated. Labeled structures include the right ventricle 1005 (RV); left ventricle 1010 (LV); and aorta 1015 (Ao).

Figure 11:
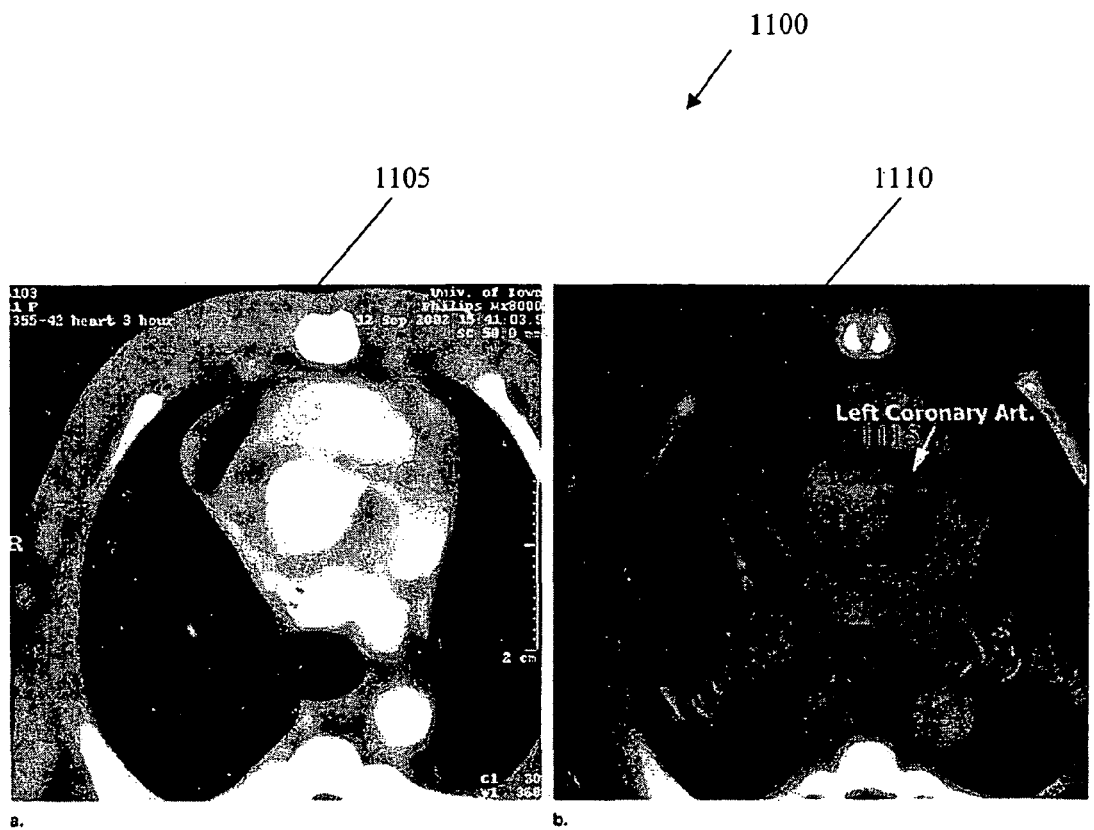
FIG. 11 shows an example image 1100 of the left coronary artery of the rabbit under high magnification.

FIG. 11 shows images 1100 of the left coronary artery of a rabbit under high magnification conditions at 3 hours after the second injection of the liposomal iohexol formulation. The left panel 1105 shows a 1.3 mm thick CT slice of in vivo rabbit heart imaged 3 hours 18 minutes after the second injection of one embodiment of liposomal iohexol. The right panel 1110 shows a volume rendered view of the same data set. The left coronary artery (shown as 1115 in 1110) was enhanced by 109 HU.

Example 7

Preparation of PEGylated Liposomes Containing Iohexol or Iodixanol

Example liposomal formulations were produced as follows. Iohexol or iodixanol solutions of approximately 350 mg I/ml were concentrated by rotary evaporation to concentrations of approximately 400-450 mg I/ml. The iohexol or iodixanol solutions were then used to prepare liposomes as described in Example 1. The suspensions of liposomes that were obtained were then extruded through a series of nucleopore track-etch membranes to obtain uniformly sized 100 nm liposomes, as described in Example 1. The liposome suspensions were then cleaned and the liposomes concentrated approximately 2.5-fold by diafiltration using Microkros® modules of 100,000 Dalton cutoff. Liposome suspensions with iodine concentrations of between 85 and 100 mg I/ml were obtained.

Example 8

In Vivo Images of Heart and Tumor in a Mouse After Administration of PEGylated Liposomes Containing Iohexol Imaging of the mouse used a specially constructed micro CT system. In this system, the animal is vertically positioned in a rotatable cradle and a stationary X-ray source and detector are used. In the system, there is a high flux rotating anode X-ray tube (Philips SRO 09 50) with a dual 0.3/1.0 mm focal spot. The flux from the system is sufficient to support exposures as short as 10 ms to limit the motion blur from the heart. A high-resolution detector with 50×50 micron pixels covering an image matrix of 2048×2048 (Microphotonics X-ray Image Star camera, Photonics Science, East Sussex, UK) was used over an active area input of 106×106 mm. A hardware feature was used that combines pixels to a 2×2 array that reduced the effective detector pitch to 100 microns.

Imaging was performed using the following X-ray parameters: typically 80 kVp, 170 mA, and 10 ms. Projections were acquired over a circular orbit of 1900 (i.e. 1800+fan angle) with a step angle of 0.50 using a total of 260 projections. Each projection set took approximately 8-10 minutes to acquire. Scanning was done with the animal placed at a source-toobject distance (sod=400 mm), an object-to-detector distance (odd=40 mm), and a source-to-detector distance (sdd=440 mm), resulting in a geometric blur of the focal spot that matched the Nyquist sample at the detector. This resulted in measured exposure for each image set of 17.64 R.

These projection images were used to reconstruct tomograms with a Feldkamp algorithm using Parker weighting. For this purpose, Cobra EXXIM software package (EXXIM Computing Corp, Livermore, Calif.) was used. Data were reconstructed as isotropic 1024×1024×1024 arrays with effective digital sampling in the image plane of 90 microns, since the magnification factor for the used geometry was 1.1.

All datasets were acquired with ventilatory synchronization (on end expiration) and cardiac gating on different points of the ECG cycle. Both temperature (36.5±1° C.) and heart rate (RR=90-100 ms) were relatively stable during the imaging studies.

Figure 12:
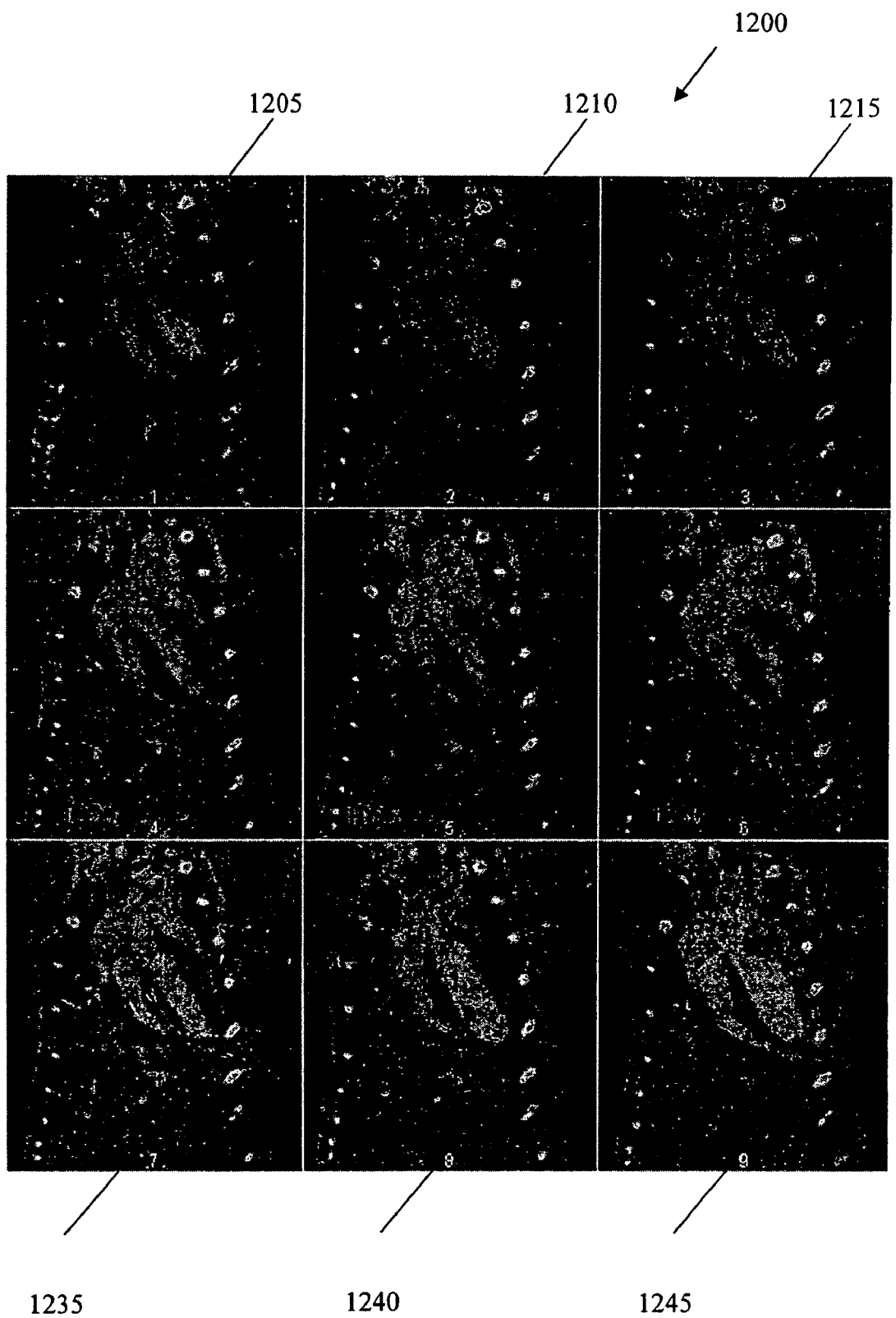
FIG. 12 shows example time-lapse coronal images 1200 of a mouse heart obtained by micro CT at 10 millisecond intervals 1205, 1210, 1215, 1220, 1225, 1230, 1235, 1240, 1245.

To perform the studies, one-half milliliter of a liposome suspension as described in Example 7 was injected into the tail vein of a mouse. Imaging and image reconstruction were performed as described above. The data indicated a stable opacification of 700 HU in the blood. The stable opacification facilitated, for example, cardiac and respiratory gated imaging, allowing time-lapse images. Example time-lapse coronal images 1200 of the mouse heart, taken at 10 millisecond intervals, are illustrated in FIG. 12. Enhancement of the cardiac chambers is visible.

Figure 13:
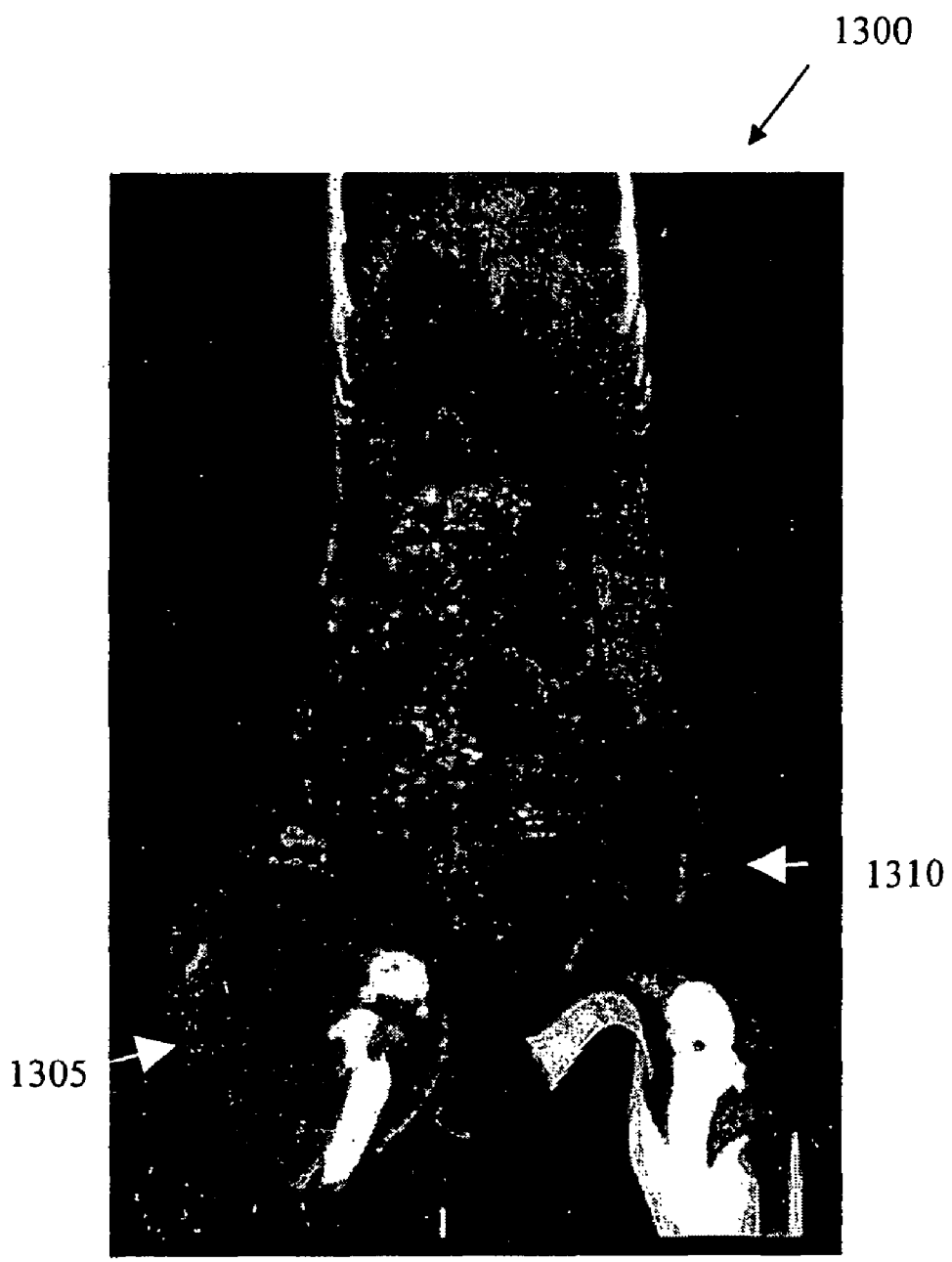
FIG. 13 shows an example image 1300, obtained by micro CT, of the abdominal region of a nude mouse containing a tumor (human squamous cell carcinoma) 1305 in the right flank and an inflamed lymph node 1310 on the left side.

In another study, a liposome suspension as described in Example 7 was injected into a nude mouse into which had been implanted a human squamous cell carcinoma (FaDu) in the right flank. FIG. 13 illustrates a micro CT coronal image 1300 of the abdominal region of the mouse 4 hours after injection of the liposome suspension. The tumor 1305 is visible in the illustrated image as is vasculature in the tumor and graded opacification in the tissue surrounding the vessels. Also visible is extravasation (leakage of blood from the vessels into the tissue) of the blood in the tumor. The positions of vessels in the tumor, and nonvascularized portions of the tumor (in the center) were confirmed by histological examination after necropsy. Also visible is an inflamed lymph node (metastatic) 1310 on the left side of the mouse.

The above descriptions have referred to the preferred embodiments and selected alternate embodiments. Modifications and alterations will become apparent to persons skilled in the art upon reading and understanding the preceding detailed description. It is intended that the embodiments described herein be construed as including all such alterations and modifications insofar as they come within the scope of the appended claims or the equivalence thereof.

We claim:

1. A method for imaging a subject, comprising introducing a composition into the bloodstream of the subject, wherein the composition comprises liposomes, the liposomes comprising:
    at least one first lipid or phospholipid;
    at least one second lipid or phospholipid which is derivatized with one or more polymers; and
    at least one sterically bulky excipient capable of stabilizing the liposomes;
    wherein the average diameter of the liposomes is less than about 150 nanometers, and wherein the liposomes encapsulate at least one iodinated nonradioactive contrast enhancing agent.

2. A method for imaging a subject, comprising:
    introducing into the bloodstream of a subject a composition comprising liposomes comprising a phospholipid, a phospholipid which is derivatized with a polymer, and cholesterol, and encapsulating one or more iodinated nonradioactive contrast enhancing agents, and wherein the liposomes have an average diameter of less than 150 nm; and
    generating images of a region of interest in the subject, wherein the iodinated nonradioactive contrast enhancing agents cause a contrast enhancement in the region of interest of at least 50 Hounsfield units for a duration of longer than five minutes.

3. The method of claim 2, wherein the generating images comprises acquiring one or more images by computed tomography.

4. The method of claim 3, wherein the images are used for one or more of detection, quantification, characterization, classification, and monitoring of ischemia and/or myocardial microcirculatory insufficiencies.

* * * * *